US010194849B2

(12) United States Patent
Otani

(10) Patent No.: US 10,194,849 B2
(45) Date of Patent: Feb. 5, 2019

(54) ENDOSCOPE SYSTEM AND METHOD FOR OPERATING THE SAME

(71) Applicant: FUJIFILM Corporation, Tokyo (JP)

(72) Inventor: Kenichi Otani, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 385 days.

(21) Appl. No.: 15/200,472

(22) Filed: Jul. 1, 2016

(65) Prior Publication Data

US 2017/0014055 A1 Jan. 19, 2017

(30) Foreign Application Priority Data

Jul. 14, 2015 (JP) .................. 2015-140807

(51) Int. Cl.
*A61B 5/1459* (2006.01)
*A61B 1/04* (2006.01)
(Continued)

(52) U.S. Cl.
CPC ........ *A61B 5/1459* (2013.01); *A61B 1/00006* (2013.01); *A61B 1/00009* (2013.01); *A61B 1/00045* (2013.01); *A61B 1/043* (2013.01); *A61B 1/045* (2013.01); *A61B 1/0638* (2013.01); *A61B 1/0646* (2013.01);
(Continued)

(58) Field of Classification Search
CPC ......... H04N 2005/2255; H04N 5/2256; H04N 5/225; A61B 1/00009; A61B 1/07; A61B 1/00045; A61B 1/043; A61B 1/0638; A61B 1/0646; A61B 1/00006; A61B 5/1459;
(Continued)

(56) References Cited

U.S. PATENT DOCUMENTS

2013/0030268 A1    1/2013   Saito

FOREIGN PATENT DOCUMENTS

JP    2013-22341 A    2/2013

OTHER PUBLICATIONS

Extended European Search Report, dated Dec. 12, 2016, for European Application No. 16178222.2.

*Primary Examiner* — Dave Czekaj
*Assistant Examiner* — Berteau Joisil
(74) *Attorney, Agent, or Firm* — Birch, Stewart, Kolasch & Birch, LLP

(57) ABSTRACT

A control section performs first preliminary imaging in which an observation target is illuminated with first blue light at a wavelength band of 450±10 nm and an image of the observation target is captured. A yellow pigment concentration calculator calculates concentration of the yellow pigment based on an image signal obtained by performing the first preliminary imaging. A prescribed exposure amount calculator calculates a prescribed exposure amount of second blue light at a wavelength band of 470±10 nm for second preliminary imaging based on the calculated concentration of the yellow pigment. A control section performs second preliminary imaging in which an observation target is illuminated with the second blue light and an image of the observation target is captured based on a prescribed exposure amount of the second blue light for the second preliminary imaging. An arithmetic value calculator calculates an arithmetic value based on an image signal obtained by performing the second preliminary imaging. A determination section determines whether or not the arithmetic value has become closer to an optimum value.

20 Claims, 15 Drawing Sheets

(51) Int. Cl.
*A61B 1/06* (2006.01)
*A61B 1/00* (2006.01)
*A61B 1/045* (2006.01)
*H04N 5/225* (2006.01)
*A61B 1/07* (2006.01)
*A61B 5/1455* (2006.01)

(52) U.S. Cl.
CPC .............. *A61B 1/0653* (2013.01); *A61B 1/07* (2013.01); *H04N 5/2256* (2013.01); *A61B 5/14556* (2013.01); *H04N 2005/2255* (2013.01)

(58) Field of Classification Search
CPC ........... A61B 1/04; A61B 1/00; A61B 5/1455; A61B 1/045; A61B 1/06
See application file for complete search history.

| ILLUMINATION LIGHT | IMAGE CAPTURING (IMAGE SIGNAL) |
|---|---|
| FIRST BLUE LIGHT BS<br>GREEN LIGHT G<br>RED LIGHT R | (Bc, Gc, Rc) |

FIG. 6

| ILLUMINATION LIGHT | | IMAGE CAPTURING (IMAGE SIGNAL) | |
|---|---|---|---|
| FIRST PRELIMINARY LIGHT EMISSION | FIRST BLUE LIGHT BS<br><br>GREEN NARROWBAND LIGHT Gn | FIRST PRELIMINARY IMAGE CAPTURING | (Bp, Gp, Rp) |
| SECOND PRELIMINARY LIGHT EMISSION | SECOND BLUE LIGHT BL<br><br>GREEN NARROWBAND LIGHT Gn | SECOND PRELIMINARY IMAGE CAPTURING | (Bq, Gq, Rq) |

FIG. 7

| ILLUMINATION LIGHT | | IMAGE CAPTURING (IMAGE SIGNAL) | |
|---|---|---|---|
| FIRST MAIN LIGHT EMISSION | SECOND BLUE LIGHT BL | FIRST MAIN IMAGE CAPTURING | (B1, G1, R1) |
| SECOND MAIN LIGHT EMISSION | FIRST BLUE LIGHT BS<br>GREEN NARROWBAND LIGHT Gn<br>RED LIGHT R | SECOND MAIN IMAGE CAPTURING | (B2, G2, R2) |

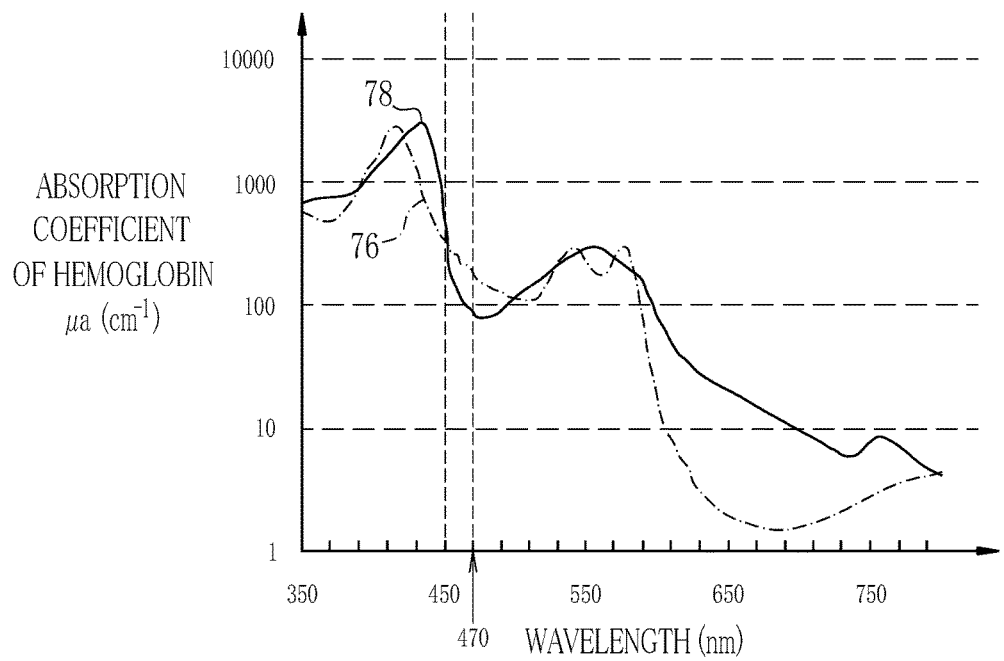
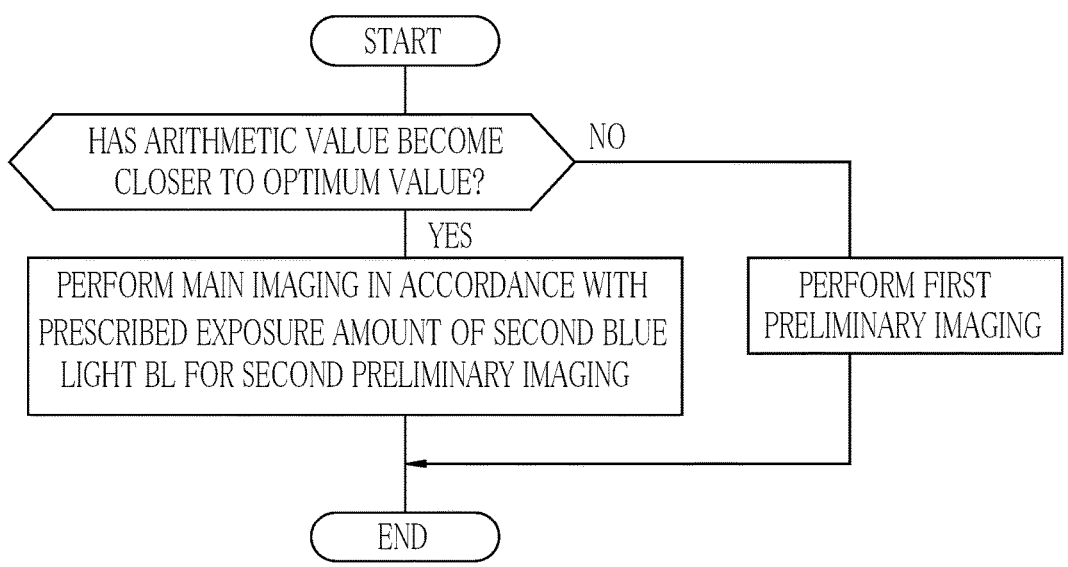

| ILLUMINATION LIGHT | | IMAGE CAPTURING (IMAGE SIGNAL) | |
|---|---|---|---|
| FIRST PRELIMINARY LIGHT EMISSION | FIRST BLUE LIGHT BS<br><br>GREEN NARROWBAND LIGHT Gn | FIRST PRELIMINARY IMAGE CAPTURING | (Bp, Gp) |
| SECOND PRELIMINARY LIGHT EMISSION | SECOND BLUE LIGHT BL<br><br>GREEN NARROWBAND LIGHT Gn | SECOND PRELIMINARY IMAGE CAPTURING | (Bq, Gq) |

ENDOSCOPE SYSTEM AND METHOD FOR OPERATING THE SAME

CROSS-REFERENCE TO RELATED APPLICATIONS

The present application claims priority under 35 U.S.C. § 119 to Japanese Patent Application No. 2015-140807, filed Jul. 14, 2015. Each of the above application(s) is hereby expressly incorporated by reference, in its entirety, into the present application.

BACKGROUND OF THE INVENTION

1. Field of the Invention

The present invention relates to an endoscope system that calculates an oxygen saturation level of an observation target, and a method for operating the endoscope system.

2. Description Related to the Prior Art

In medical fields, diagnoses using an endoscope system that includes a light source device, an endoscope, and a processor device are widely performed. In particular, an endoscope system capable of obtaining an observation image, in which specific tissues and structures such as blood vessels and a glandular structure are emphasized, has been developed by not only capturing an image of an observation target but also adjusting a wavelength of illumination light for illuminating the observation target and subjecting an image signal obtained by capturing an image of the observation target to signal processing such as spectroscopic estimation processing.

Further, in recent years, there has been used an endoscope system that acquires biological function information based on an image signal obtained by capturing an image of an observation target so as to make a diagnosis on a lesion. As the biological function information, an oxygen saturation level of hemoglobin in blood is used, for example, as described in United States Patent Application Publication No. 2013/0030268 (corresponding to Japanese Patent Application Laid-Open No. 2013-22341). According to a method for obtaining the oxygen saturation level described in United States Patent Application Publication No. 2013/0030268, light having a wavelength at which an absorption coefficient of oxygenated hemoglobin is different from an absorption coefficient of reduced hemoglobin is used as measurement light for the oxygen saturation level, and a correlation between a plurality of image signals including at least an image signal obtained during illumination of the measurement light and the oxygen saturation level is used, so as to calculate the oxygen saturation level.

The correlation between a plurality of the image signals and the oxygen saturation level as described above may vary depending on various sites such as esophagus, stomach, and large intestine, a gender, an age, and the like, which are different for each patient, in some cases. As a countermeasure against this problem, according to United States Patent Application Publication No. 2013/0030268, before observing a body cavity with use of the oxygen saturation level, preliminary measurement of the oxygen saturation level is performed based on the image signal obtained by capturing an image of a normal part of the observation target, and the correlation is corrected based on the oxygen saturation level obtained by the preliminary measurement and an oxygen saturation level of the normal part as a standard level. Since the correction of the correlation as described above is performed, it becomes possible to calculate the oxygen saturation level regardless of the sites and the patients.

The calculation accuracy of the oxygen saturation level is decreased due to the difference in the sites and the patients as described above. Additionally, the calculation accuracy of the oxygen saturation level also may be decreased in the case where the observation target has yellow (or brownish yellow) pigment of bilirubin, stercobilin, or the like. Therefore, the observation target is cleaned in order to remove mucus or the like having the yellow pigment before calculation of the oxygen saturation level. However, it is difficult to completely remove the mucus or the like having the yellow pigment. Further, the mucus or the like having the yellow pigment may be newly secreted during the observation in some cases. Accordingly, in the case where the preliminary measurement as described in United States Patent Application Publication No. 2013/0030268 is performed in a state that the observation target has the yellow pigment, the correlation is corrected based on the image signal that has been influenced by the yellow pigment or the like, and therefore it is difficult to calculate the oxygen saturation level with a high degree of accuracy.

SUMMARY OF THE INVENTION

An object of the present invention is to provide an endoscope system capable of calculating an oxygen saturation level with a high degree of accuracy even in a state that an observation target has yellow pigment or the like, and a method for operating the endoscope system.

In order to achieve the above and other objects, an endoscope system of the present invention includes a light source, an image capturing sensor, a control section, a yellow pigment concentration calculator, a prescribed exposure amount calculator, an arithmetic value calculator, and a determination section. The light source emits first light at a first wavelength band in which a light absorption amount changes in accordance with a concentration of yellow pigment contained in an observation target, and second light at a second wavelength band in which a light absorption amount changes in accordance with an oxygen saturation level of hemoglobin contained in the observation target and the light absorption amount also changes in accordance with the concentration of the yellow pigment. The second wavelength band is longer than the first wavelength band. The image capturing sensor captures an image of the observation target. The control section controls at least one of the light source and the image capturing sensor, so as to perform first preliminary imaging for capturing an image of the observation target illuminated with the first light for the first preliminary imaging and perform second preliminary imaging for capturing an image of the observation target illuminated with the second light for the second preliminary imaging. The yellow pigment concentration calculator calculates the concentration of the yellow pigment based on a first image signal obtained by performing the first preliminary imaging. The prescribed exposure amount calculator calculates a prescribed exposure amount of the second light in the second preliminary imaging based on the calculated concentration of the yellow pigment. The arithmetic value calculator performs a specific calculation based on a second image signal obtained by performing the second preliminary imaging in accordance with the prescribed exposure amount of the second light, so as to calculate an arithmetic value. The determination section determines whether or not the arithmetic value has become closer to an optimum value specified in advance.

It is preferable that the control section performs main imaging for capturing an image of the observation target illuminated with the second light for the main imaging in accordance with the prescribed exposure amount of the second light in the case where it is determined that the arithmetic value has become closer to the optimum value. It is preferable that an oxygen saturation level calculator calculates the oxygen saturation level based on a third image signal obtained by performing the main imaging. It is preferable that an image generator generates an oxygen saturation image in which the oxygen saturation level is represented based on the oxygen saturation level calculated by the oxygen saturation level calculator and the third image signal.

It is preferable that the endoscope system further includes a mode switching section for switching to an oxygen saturation mode for calculating the oxygen saturation level and generating the oxygen saturation image. It is preferable that the control section performs the first preliminary imaging and the second preliminary imaging in the case where the switching to the oxygen saturation mode is performed.

It is preferable that the endoscope system further includes a still-image acquisition instructing section for outputting instructions for acquiring the oxygen saturation image as a still image. It is preferable that the control section performs the first preliminary imaging and the second preliminary imaging in the case where the instructions for acquiring the still image are outputted.

It is preferable that the control section performs the first preliminary imaging and the second preliminary imaging while a moving image of the observation target based on the oxygen saturation image is displayed.

It is preferable that the control section controls such that an illumination time for illuminating the observation target in the first preliminary imaging and the second preliminary imaging is shorter than an illumination time for illuminating the observation target in the main imaging.

It is preferable that the image capturing sensor includes a plurality of pixels containing specific pixels each of which is sensitive to at least one of the first wavelength band and the second wavelength band. It is preferable that the control section reads out a signal from the specific pixels without reading a signal from pixels other than the specific pixels among a plurality of the pixels in the case where the first preliminary imaging and the second preliminary imaging are performed.

It is preferable that the control section controls at least one of a light emission amount of the second light in the second preliminary imaging and an exposure time of the image capturing sensor in the second preliminary imaging in accordance with the prescribed exposure amount of the second light.

It is preferable that the prescribed exposure amount calculator increases the prescribed exposure amount of the second light in the second preliminary imaging, as the concentration of the yellow pigment calculated by the yellow pigment concentration calculator becomes higher.

It is preferable that the optimum value is a value obtained in the case where the observation target does not have the yellow pigment.

Preferably, the light source emits third light at a third wavelength band in which a light absorption amount changes in accordance with a blood volume, and the third wavelength band is longer than each of the first wavelength band and the second wavelength band. It is preferable that the control section captures an image of the observation target illuminated with the first light for the first preliminary imaging and the third light in the first preliminary imaging, and captures an image of the observation target illuminated with the second light for the second preliminary imaging and the third light in the second preliminary imaging. It is preferable that the prescribed exposure amount calculator calculates the prescribed exposure amount of at least one of the second light and the third light in the second preliminary imaging. It is preferable that the arithmetic value calculator calculates the arithmetic value based on the second image signal obtained by performing the second preliminary imaging in accordance with the prescribed exposure amount of at least one of the second light and the third light.

It is preferable that the specific calculation is to calculate a signal ratio of an image signal obtained by capturing an image of the observation target illuminated with the second light to an image signal obtained by capturing an image of the observation target illuminated with the third light out of the second image signal obtained by performing the second preliminary imaging.

It is preferable that the control section causes the first light and the third light to be emitted in a sequential manner in the first preliminary imaging, and causes the second light and the third light to be emitted in a sequential manner in the second preliminary imaging.

It is preferable that the control section causes the first light and the third light to be emitted at the same time in the first preliminary imaging, and causes the second light and the third light to be emitted at the same time in the second preliminary imaging.

It is preferable that the third light is narrowband light. Further, it is preferable that the third light is generated by restricting a wavelength band of the broadband light.

It is preferable that the prescribed exposure amount calculator decreases the prescribed exposure amount of the third light in the second preliminary imaging, as the concentration of the yellow pigment calculated by the yellow pigment concentration calculator becomes higher.

It is preferable that the first wavelength band includes an isosbestic wavelength at which oxygenated hemoglobin and reduced hemoglobin have the same absorption coefficient.

It is preferable that the first wavelength band is 450±10 nm, the second wavelength band is 470±10 nm, and the third wavelength band is 540±20 nm.

A method for operating an endoscope system of the present invention includes the steps of: emitting first light at a first wavelength band in which a light absorption amount changes in accordance with a concentration of yellow pigment contained in an observation target, and second light at a second wavelength band in which a light absorption amount changes in accordance with an oxygen saturation level of hemoglobin contained in the observation target and the light absorption amount also changes in accordance with the concentration of the yellow pigment, from a light source, the second wavelength band being longer than the first wavelength band; capturing an image of the observation target by an image capturing sensor; controlling at least one of the light source and the image capturing sensor by a control section, so as to perform first preliminary imaging for capturing an image of the observation target illuminated with the first light for the first preliminary imaging and perform second preliminary imaging for capturing an image of the observation target illuminated with the second light for the second preliminary imaging; calculating the concentration of the yellow pigment based on a first image signal obtained by performing the first preliminary imaging by a yellow pigment concentration calculator; calculating a prescribed exposure amount of the second light in the second preliminary imaging based on the calculated concentration of the yellow pigment by a prescribed exposure amount calculator; performing a specific calculation based on a second image signal obtained by performing the second preliminary imaging in accordance with the prescribed exposure amount of the second light so as to calculate an arithmetic value by an arithmetic value calculator; and determining whether or not the arithmetic value has become closer to an optimum value specified in advance by a determination section.

According to the present invention, even in a state that the observation target has yellow pigment or the like, it is possible to calculate the oxygen saturation level with a high degree of accuracy.

BRIEF DESCRIPTION OF THE DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein:

FIG. 6 illustrates illumination light and image capturing of an observation target in first preliminary imaging and second preliminary imaging in an oxygen saturation mode;

FIG. 7 illustrates illumination light and image capturing of an observation target in main imaging in the oxygen saturation mode;

FIG. 10 is a graph illustrating an absorption coefficient of each of oxygenated hemoglobin and reduced hemoglobin;

FIG. 11 is a flowchart illustrating a procedure of determining whether or not to perform the main imaging;

DETAILED DESCRIPTION OF THE PREFERRAL EMBODIMENT(S) OF THE PRESENT INVENTION

First Embodiment

Figure 1:
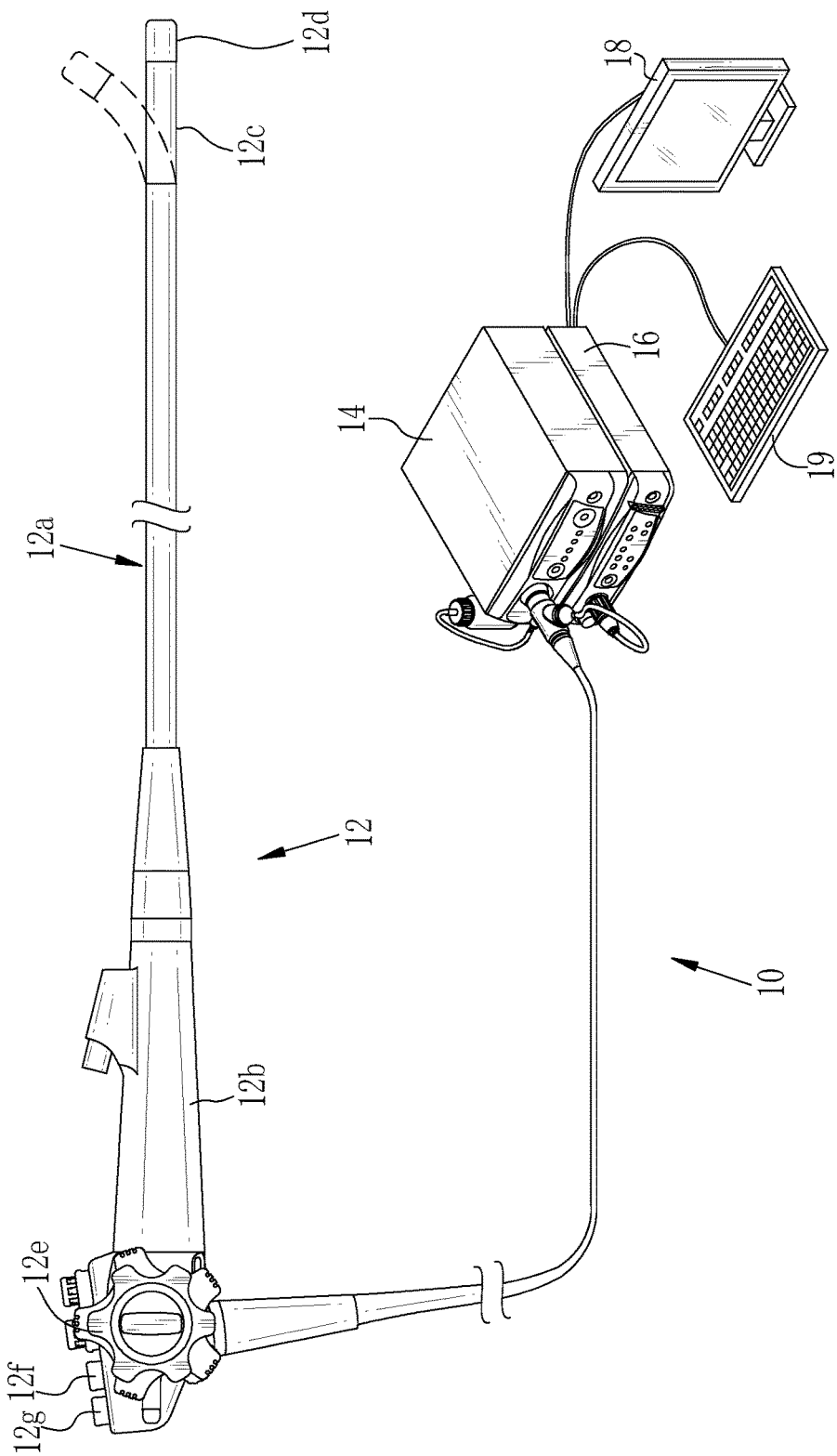
FIG. 1 is an external view of an endoscope system.

In FIG. 1, an endoscope system 10 includes an endoscope 12, a light source device 14, a processor device 16, a monitor 18, and a console 19. The endoscope 12 is optically connected to the light source device 14, and electrically connected to the processor device 16. The endoscope 12 includes an insertion section 12a to be inserted into a body cavity of an observation target, a control handle unit 12b provided at a proximal end of the insertion section 12a, a flexible portion 12c provided on a distal side of the insertion section 12a, and a distal end portion 12d. The control handle unit 12b includes an angle knob 12e to be used to bend the flexible portion 12c. The flexible portion 12c is bent by operating the angle knob 12e, and thereby the distal end portion 12d is directed to a desired direction. The distal end portion 12d has a jet orifice (not shown in the drawings) through which a cleaning fluid is sprayed toward the observation target.

Further, the control handle unit 12b includes, in addition to the angle knob 12e, a mode switching section 12f to be used for the switching operation of the observation modes, and a still-image acquisition instructing section 12g for outputting instructions for acquiring a still image of the observation target.

The endoscope system 10 has two observation modes, i.e., a normal mode and an oxygen saturation mode. In the normal mode, white light is used as illumination light at the time of capturing an image of the observation target to acquire an image which possess a natural color (hereinafter, referred to as normal image), and the normal image is displayed on the monitor 18. In the oxygen saturation mode, the oxygen saturation level of the observation target is measured, and an image in which the measured oxygen saturation level is visualized using pseudo color or the like (hereinafter referred to as oxygen saturation image) is displayed on the monitor 18.

Additionally, in the oxygen saturation mode, a preliminary imaging mode is executed in the case where the normal mode is switched to the oxygen saturation mode, and a main imaging mode is executed after the completion of the preliminary imaging mode. The preliminary imaging mode means an imaging mode in which a prescribed exposure amount for use in the main imaging mode is determined based on an image signal obtained by imaging the observation target before the main imaging mode. The main imaging mode means an imaging mode in which a correlation between an image signal obtained by imaging the observation target in accordance with the prescribed exposure amount determined in the preliminary imaging mode and the oxygen saturation level is used to calculate the oxygen saturation level of the observation target, and the oxygen saturation image representing the oxygen saturation level is displayed.

The processor device 16 is electrically connected to the monitor 18 and the console 19. The image of the observation target and image information incidental to the image of the observation target are displayed on the monitor 18. The console 19 functions as a UI (user interface) for receiving input operation of function settings and the like. Note that, an external storage (not shown in the drawings) for storing images, image information, and the like may be connected to the processor device 16.

Figure 2:
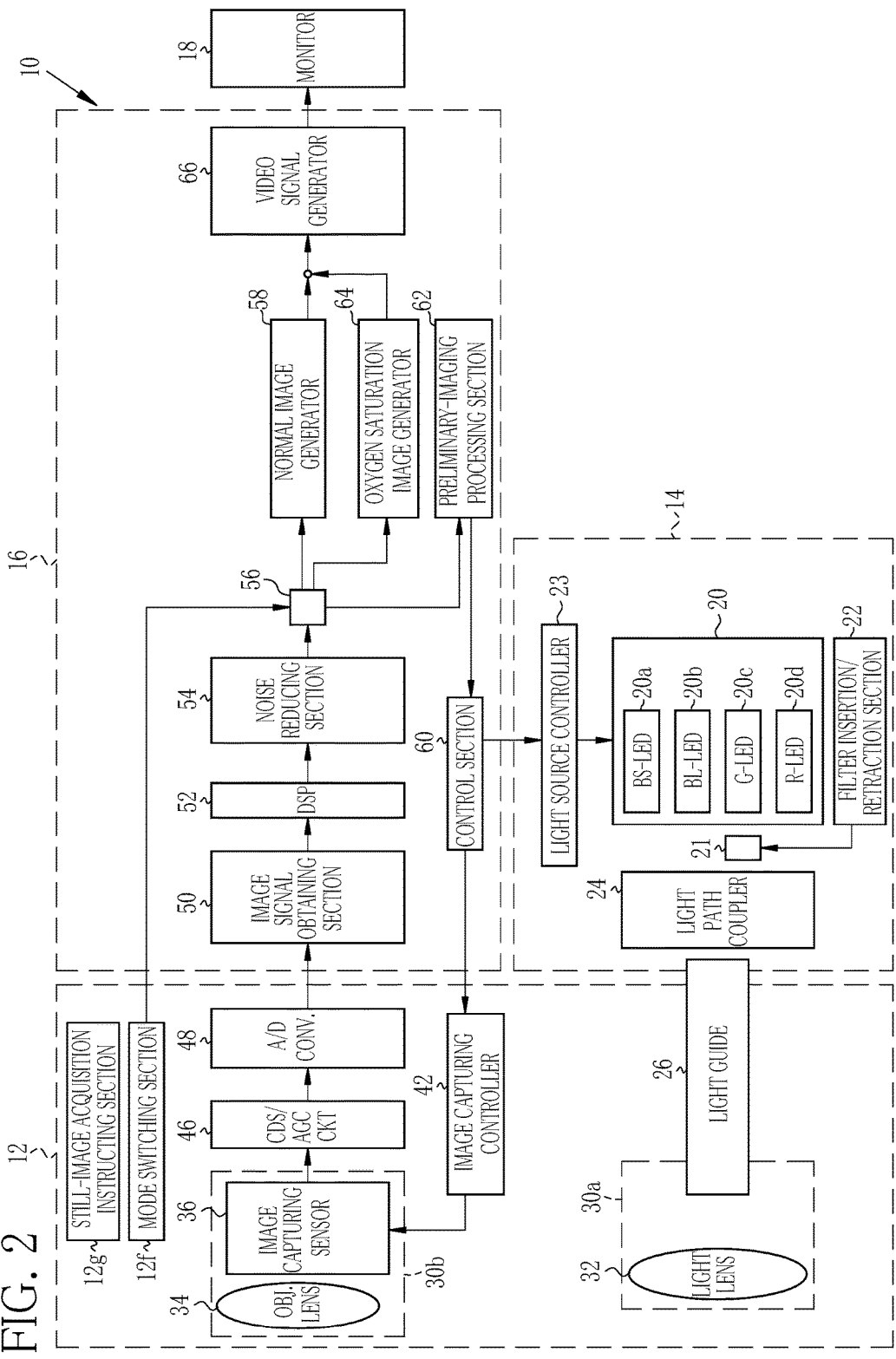
FIG. 2 is a block diagram illustrating functions of an endoscope system according to a first embodiment of the present invention.

As shown in FIG. 2, the light source device 14 includes a light source 20, a green narrowband filter 21, a filter insertion/retraction section 22, a light source controller 23, and a light path coupler 24. The light source 20 includes, for example, a plurality of semiconductor light sources, and turns on or off each of the semiconductor light sources. When the light source 20 is turned on, illumination light for illuminating the observation target is emitted. In this embodiment, the light source 20 is provided with 4 color LEDs including a BS-LED (Blue Short-wavelength Light Emitting Diode) 20a, a BL-LED (Blue Long-wavelength Light Emitting Diode) 20b, a G-LED (Green Light Emitting Diode) 20c, and an R-LED (Red Light Emitting Diode) 20d.

The BS-LED 20a emits first blue light BS (corresponding to "first light" of the present invention) at a wavelength band of 450±10 nm (corresponding to "first wavelength band" of the present invention). The BL-LED 20b emits second blue light BL (corresponding to "second light" of the present invention) at a wavelength band of 470±10 nm (corresponding to "second wavelength band" of the present invention) which is longer than that of the first blue light BS. The G-LED 20c emits green light G at a wavelength band in the range of 500 nm to 600 nm. The R-LED 20d emits red light R at a wavelength band of 640±20 nm. Note that, a center wavelength and a peak wavelength of the light of each color may be the same or different.

The green narrowband filter 21 is disposed between the G-LED 20c and the light path coupler 24. The green narrowband filter 21 restricts the wavelength band of the green light G emitted from the G-LED 20c to the wavelength band of 540±20 nm (corresponding to "third wavelength band" of the present invention), so as to generate green narrowband light Gn (corresponding to "third light" of the present invention). The filter insertion/retraction section 22 is controlled by the light source controller 23, so as to retract the green narrowband filter 21 from a light path of the green light G in the normal mode and insert the green narrowband filter 21 into the light path of the green light G in the oxygen saturation mode.

The light source controller 23 inputs a control signal to each of the LEDs 20a to 20d independently, so as to control the turning on/off of each of the LEDs 20a to 20d and an emission amount of each of the LEDs 20a to 20d at the time of turning on each of the LEDs 20a to 20d independently. The control of the turning on/off of each of the LEDs 20a to 20d by the light source controller 23 is performed differently depending on the observation modes. In the normal mode, the light source controller 23 emits the first blue light BS, the green light G, and the red light R at the same time by turning on the BS-LED 20a, the G-LED 20c, and the R-LED 20d at the same time.

In contrast, in the oxygen saturation mode, the light source controller 23 controls the light emission in a different manner between the preliminary imaging mode and the main imaging mode. For example, the light source controller 23 performs first preliminary light emission for emitting at least the first blue light BS and a second preliminary light emission for emitting at least the second blue light BL in the preliminary imaging mode. Further, the light source controller 23 performs first main light emission for emitting the second blue light BL and second main light emission for emitting the first blue light BS, the green narrowband light Gn, and the red light R, alternately, in the main imaging mode.

Specifically, in the case where the first preliminary light emission is performed in the preliminary imaging mode, the light source controller 23 emits the first blue light BS and the green narrowband light Gn at the same time by turning on the BS-LED 20a and the G-LED 20c at the same time. Further, in the case where the second preliminary light emission is performed, the light source controller 23 emits the second blue light BL and the green narrowband light Gn at the same time by turning on the BL-LED 20b and the G-LED 20c at the same time.

In the case where the first main light emission is performed in the main imaging mode, the light source controller 23 emits the second blue light BL by turning on the BL-LED 20b. In the case where the second main light emission is performed, the light source controller 23 emits the first blue light BS, the green narrowband light Gn, and the red light R at the same time by turning on the BS-LED 20a, the G-LED 20c, and the R-LED 20d at the same time. Note that, in this embodiment, the light source controller 23 controls such that the illumination time of the first main light emission in the main imaging mode becomes shorter than the illumination time of the first preliminary light emission in the preliminary imaging mode, and the illumination time of the second main light emission in the main imaging mode becomes shorter than the illumination time of the second preliminary light emission in the preliminary imaging mode.

The light path coupler 24 consists of a mirror, a lens, and the like, and makes the light emitted from each of the LEDs 20a to 20d incident on a light guide 26. The light guide 26 is incorporated in the endoscope 12 and a universal cord. The universal cord is a cord for connecting the endoscope 12 to the light source device 14 and the processor device 16. The light guide 26 propagates the light from the light path coupler 24 to the distal end portion 12d of the endoscope 12.

The distal end portion 12d of the endoscope 12 is provided with an illumination optical system 30a and an image capturing optical system 30b. The illumination optical system 30a has a light lens 32. Through the light lens 32, the observation target is illuminated with the illumination light from the light guide 26. The image capturing optical system 30b has an objective lens 34 (abbreviated as obj. lens in the drawings) and an image capturing sensor 36. The objective lens 34 makes the light, which is returned from the observation target illuminated with the illumination light, incident on the image capturing sensor 36. Thereby, an image of the observation target is formed on the image capturing sensor 36.

Figure 3:
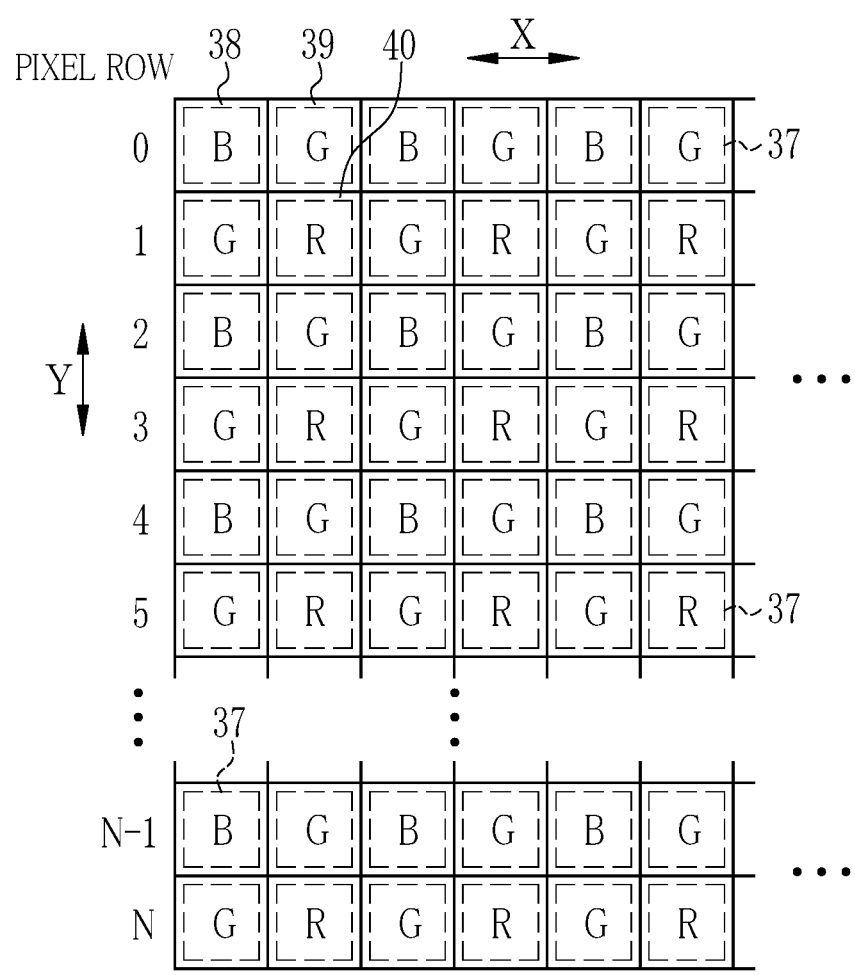
FIG. 3 illustrates a pixel array of an image capturing sensor.

The image capturing sensor 36 is a color image capturing sensor which captures an image of the observation target illuminated with the illumination light and outputs an image signal. As shown in FIG. 3, a plurality of pixels 37 are arranged in a matrix in two dimensions, in a row direction (X direction) and a column direction (Y direction) on an image capturing surface of the image capturing sensor 36. Any one of a B (blue) color filter 38, a G (green) color filter 39, and an R (red) color filter 40 is provided to one pixel 37. The color filters 38 to 40 are arranged in a Bayer pattern, in which the G color filters 39 are arranged in an alternate checkered pattern over the corresponding pixels and the B and R color filters 38 and 40 are arranged over the remaining pixels such that the B color filters 38 and R color filters 40 form respective square lattice patterns.

Hereinbelow, the pixel 37 over which the B color filter 38 is disposed is referred to as B pixel (blue pixel) (corresponding to "specific pixel" of the present invention), the pixel 37 over which the G color filter 39 is disposed is referred to as G pixel (green pixel), and the pixel 37 over which the R color filter 40 is disposed is referred to as R pixel (red pixel). In each of the even-numbered (0, 2, 4, N−1) pixel rows, the B and G pixels are arranged alternately. In each of the odd-numbered (1, 3, 5, . . . , N) pixel rows, the R and G pixels are arranged alternately. Here, the pixel row refers to a row of the pixels 37 that are arranged in the row direction.

Figures 4, 5:
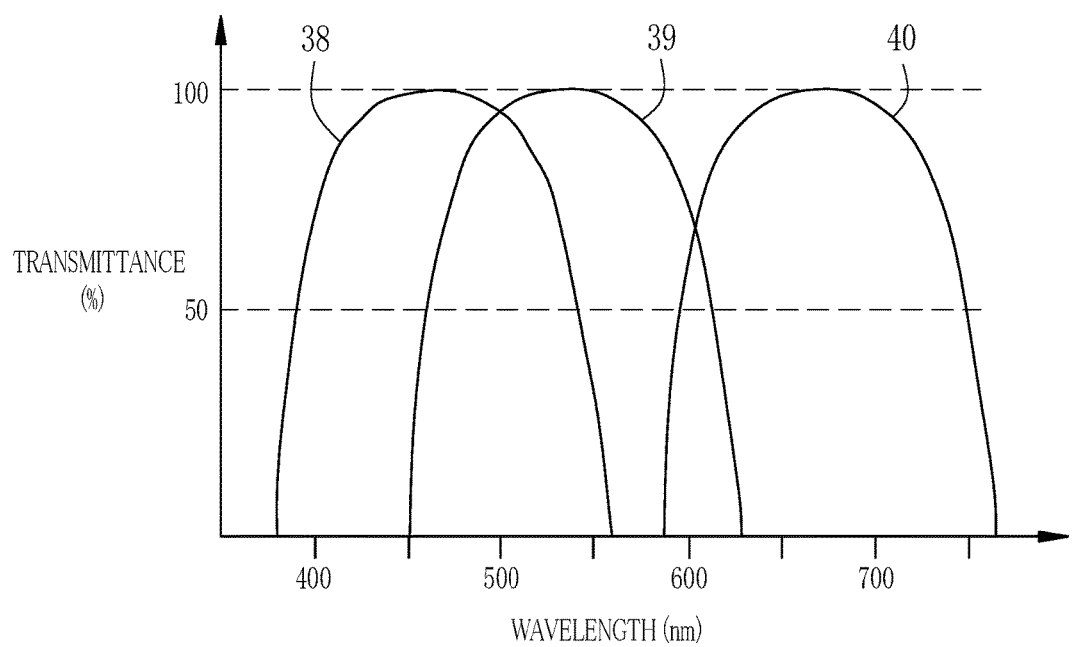
FIG. 4 is a graph illustrating spectral characteristics of color filters.
FIG. 5 illustrates illumination light and image capturing of an observation target in a normal mode.

As shown in FIG. 4, the light at the wavelength band in the range of 380 nm to 560 nm is allowed to pass through the B color filter 38. The light at the wavelength band in the range of 450 nm to 630 nm is allowed to pass through the G color filter 39. The light at the wavelength band in the range of 580 nm to 760 nm is allowed to pass through the R color filter 40. Therefore, the B pixel is sensitive to the first blue light BS at the wavelength band of 450±10 nm and the second blue light BL at the wavelength band of 470±10 nm. The G pixel is sensitive to the green light G at the wavelength band in the range of 500 nm to 600 nm and the green narrowband light Gn at the wavelength band of 540±20 nm. The R pixel is sensitive to the red light R at the wavelength band of 640±20 nm.

As the image capturing sensor 36, a CCD (Charge Coupled Device) image capturing sensor or a CMOS (Complementary Metal-Oxide Semiconductor) image capturing sensor can be used. The readout of the image signal performed by the image capturing sensor 36 is controlled by an image capturing controller 42. The image capturing controller 42 is capable of performing an all-pixel reading method and a thin-out reading method as a signal reading method.

In the all-pixel reading method, the signals are read out sequentially on a pixel row by pixel row basis from the first pixel row "0" to the last pixel row "N". Thus, the signals are read out from all of the pixels 37 (see FIG. 3). In the thin-out reading method, the signals can be read out from the pixels of a specific color among the B, G, and R pixels. In this embodiment, the image capturing controller 42 reads out the signals by the all-pixel reading method, such that the image signals are outputted from the B, G, and R pixels, respectively.

Incidentally, instead of the image capturing sensor 36 of a primary color, a complementary-color image capturing sensor provided with complementary-color filters of C (cyan), M (magenta), Y (yellow), and G (green) may be used. In the case where the complementary-color image capturing sensor is used, since the image signals of four colors (CMYG) are outputted, the image signals of four colors (CMYG) are converted into the image signals of three colors (RGB) by conversion from complementary color to primary color, so as to obtain the image signals of RGB which are the same as those of the image capturing sensor 36.

The image capturing controller 42 and the light source controller 23 are electrically connected to each other, so as to control the imaging capturing in accordance with the light emission control performed by the light source controller 23. As shown in FIG. 5, in the normal mode, the image capturing controller 42 controls the image capturing sensor 36, such that an image of the observation target illuminated with the first blue light BS, the green light G, and the red light R emitted based on the control by the light source controller 23 is captured on a frame by frame basis. Thereby, a Bc image signal is outputted from the B pixels of the image capturing sensor 36, a Gc image signal is outputted from the G pixels of the image capturing sensor 36, and an Rc image signal is outputted from the R pixels of the image capturing sensor 36. Note that, the exposure time of the image capturing sensor 36 is synchronized with the illumination time of the illumination light by the image capturing controller 42.

In the oxygen saturation mode, the image capturing controller 42 controls the image capturing differently depending on the preliminary imaging mode and the main imaging mode. Specifically, in the preliminary imaging mode, the image capturing controller 42 performs first preliminary image capturing as shown in FIG. 6. In the first preliminary image capturing, an image corresponding to one frame of the observation target, which is being illuminated with the first blue light BS and the green narrowband light Gn emitted at the same time at the first preliminary light emission, is captured. Thereby, in the first preliminary image capturing, a Bp image signal is outputted from the B pixels of the image capturing sensor 36, a Gp image signal is outputted from the G pixels of the image capturing sensor 36, and an Rp image signal is outputted from the R pixels of the image capturing sensor 36. Note that, each of the Bp image signal, the Gp image signal, and the Rp image signal corresponds to the "first image signal" of the present invention.

Further, in second preliminary image capturing, an image corresponding to one frame of the observation target, which is being illuminated with the second blue light BL and the green narrowband light Gn emitted at the same time at the second preliminary light emission, is captured. Thereby, in the second preliminary image capturing, the Bq image signal is outputted from the B pixels of the image capturing sensor 36, the Gq image signal is outputted from the G pixels of the image capturing sensor 36, and the Rq image signal is outputted from the R pixels of the image capturing sensor 36. Note that, each of the Bq image signal, the Gq image signal, and the Rq image signal corresponds to the "second image signal" of the present invention.

In contrast, in the main imaging mode, as shown in FIG. 7, the image capturing controller 42 performs first main image capturing and second main image capturing. In the first main image capturing, an image corresponding to one frame of the observation target, which is being illuminated with the second blue light BL emitted at the first main light emission, is captured. In the second main image capturing, an image corresponding to one frame of the observation target, which is being illuminated with the first blue light BS, the green narrowband light Gn, and the red light R emitted at the same time at the second main light emission is captured.

Thereby, in the first main image capturing, a B1 image signal is outputted from the B pixels of the image capturing sensor 36, G1 image signal is outputted from the G pixels of the image capturing sensor 36, and a R1 image signal is outputted from the R pixels of the image capturing sensor 36. Further, in the second main image capturing, a B2 image signal is outputted from the B pixels of the image capturing sensor 36, a G2 image signal is outputted from the G pixels of the image capturing sensor 36, and a R2 image signal is outputted from the R pixels of the image capturing sensor 36. Note that, each of the B1, G1, R1, B2, G2, and R2 image signals corresponds to "third image signal" of the present invention.

As shown in FIG. 2, a CDS/AGC (Correlated Double Sampling/Automatic Gain Control) circuit 46 (abbreviated as CDS/AGC ckt in the drawings) subjects an analog image signal obtained by the image capturing sensor 36 to correlated double sampling (CDS) or automatic gain control (AGC). The image signal subjected to the CDS/AGC circuit 46 is converted into a digital image signal by an A/D (Analog/Digital) converter 48 (abbreviated as A/D conv. in the drawings). The digital image signal after the A/D conversion is inputted to the processor device 16.

The processor device 16 includes an image signal obtaining section 50, a DSP (Digital Signal Processor) 52, a noise reducing section 54, an image processing switching section 56, a normal image generator 58, a control section 60, a preliminary imaging processing section 62, an oxygen saturation image generator 64, and a video signal generator 66. The image signal obtaining section 50 receives the image signal from the endoscope 12, and transmits the received image signal to the DSP 52.

The DSP 52 performs various types of signal processing such as defect correction processing, offset processing, gain correction processing, linear matrix processing, gamma conversion processing, demosaicing processing, and YC conversion processing on the received image signals. In the defect correction processing, the signals of defective pixels of the image capturing sensor 36 are corrected. In the offset processing, dark current components are removed from the image signals that have been subjected to the defect correction processing, and thereby, an accurate zero level is set. In the gain correction processing performed after the offset processing, a signal level of each of the image signals is adjusted by multiplying the image signals of each color by a specific gain. In the linear matrix processing, color reproducibility of the image signals of each color, which has been subjected to the gain correction processing, is improved.

In the gamma conversion processing, brightness and saturation of each of the image signals, which has been subjected to the linear matrix processing, are adjusted. In the demosaic processing (also referred to as isotropic processing or synchronization processing), a signal of missing color of each pixel is generated so as to interpolate the image signals subjected to the gamma conversion processing. Through the demosaic processing, all the pixels have signals of RGB colors. The DSP 52 performs YC conversion processing on each image signal after the demosaic processing, and outputs a brightness signal Y and color difference signals Cb and Cr to the noise reducing section 54.

The noise reducing section 54 performs noise removal processing on the image signals from the DSP 52. The noise removal processing is, for example, a moving average method, a median filter method, or the like. The image signals, from which noise has been removed through the noise removal processing, are inputted to the image processing switching section 56.

The image processing switching section 56 switches a destination to which the image signal is transmitted from the noise reducing section 54 depending on the currently-set observation mode. Specifically, in the case where the currently-set observation mode is the normal mode, the image processing switching section 56 transmits the image signals to the normal image generator 58. In contrast, in the case where the currently-set observation mode is the oxygen saturation mode, the image processing switching section 56 transmits the image signals to the preliminary imaging processing section 62 in the preliminary imaging mode, and transmits the image signals to the oxygen saturation image generator 64 in the main imaging mode.

The normal image generator 58 further performs color conversion processing, such as 3×3 matrix processing, gradation conversion processing, and three-dimensional LUT (Look Up Table) processing, on one frame of the Rc image signal, the Gc image signal, and the Bc image signal received from image processing switching section 56. Various kinds of color enhancement processing is performed on the image data of each of the RGB colors which has been subjected to the color conversion processing. Additionally, structure enhancement processing such as spatial frequency enhancement is performed on the image data of each of the RGB colors which has been subjected to the color enhancement processing. Then, the image data of each of the RGB colors which has been subjected to the structure enhancement processing is inputted as a normal image to the video signal generator 66.

The control section 60 controls the light source controller 23 and the image capturing controller 42, so as to execute the preliminary imaging mode and the main imaging mode. The preliminary imaging mode is executed in the case where the switching to the oxygen saturation mode is performed by the mode switching section 12f. The main imaging mode is executed in the case where it is decided that the main imaging is performed based on a determination result from a determination section 75 to be described later. Note that, the control section 60 is electrically connected to the image processing switching section 56, and notifies the image processing switching section 56 of which of the preliminary imaging mode and the main imaging mode has been executed.

In the preliminary imaging mode, the control section 60 performs the first preliminary imaging and the second preliminary imaging. In the first preliminary imaging, the control section 60 controls the light source controller 23 to execute the first preliminary light emission, and controls the image capturing controller 42 to execute the first preliminary image capturing. Thereby, in the first preliminary imaging, an image of the observation target illuminated with the first blue light BS and the green narrowband light Gn is captured, such that the Bp image signal, the Gp image signal, and the Rp image signal are obtained.

Further, in the second preliminary imaging, the control section 60 controls the light source controller 23 to execute the second preliminary light emission, and controls the image capturing controller 42 to execute the second preliminary image capturing. Thereby, in the second preliminary imaging, an image of the observation target illuminated with the second blue light BL and the green narrowband light Gn is captured, such that the Bq image signal, the Gq image signal, and the Rq image signal are obtained.

In the main imaging mode, the control section 60 controls the light source controller 23 to alternately execute the first main light emission and the second main light emission, and controls the image capturing controller 42 in accordance with the first main light emission and the second main light emission, such that the first main image capturing and the second main image capturing are alternately executed. Thereby, in the case where the first main light emission and the first main image capturing are executed, an image of the observation target illuminated with the second blue light BL is captured, such that the B1 image signal, the G1 image signal, and the R1 image signal are obtained. Further, in the case where the second main light emission and the second main image capturing are executed, an image of the observation target illuminated with the first blue light BS, the green narrowband light Gn, and the red light R is captured, such that the B2 image signal, the G2 image signal, and the R2 image signal are obtained.

Figure 8:
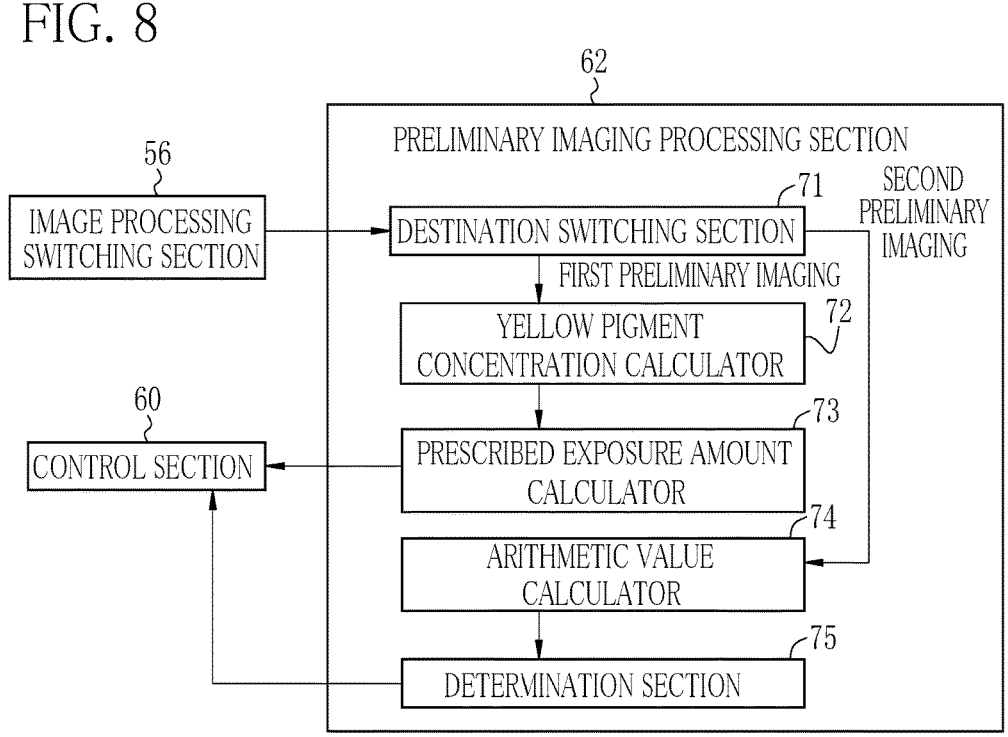
FIG. 8 is a block diagram illustrating functions of a preliminary imaging processing section.

The preliminary imaging processing section 62 is activated in the case where the control section 60 executes the preliminary imaging mode. As shown in FIG. 8, the preliminary imaging processing section 62 includes a destination switching section 71, a yellow pigment concentration calculator 72, a prescribed exposure amount calculator 73, an arithmetic value calculator 74, and the determination section 75.

The destination switching section 71 switches the destination, to which the image signal received from the image processing switching section 56 is transmitted, depending on which of the first preliminary imaging and the second preliminary imaging has been performed by the control section 60. Specifically, in the case where the first preliminary imaging is performed, the destination switching section 71 transmits the Bp image signal, the Gp image signal, and the Rp image signal obtained in the first preliminary imaging to the yellow pigment concentration calculator 72. In the case where the second preliminary imaging is performed, the destination switching section 71 transmits the Bq image signal, the Gq image signal, and the Rq image signal obtained in the second preliminary imaging to the arithmetic value calculator 74.

The yellow pigment concentration calculator 72 calculates the concentration of the yellow pigment based on the Bp image signal and the Gp image signal among the Bp image signal, the Gp image signal, and the Rp image signal which have been obtained by performing the first preliminary imaging. The yellow pigment is bilirubin or stercobilin contained in mucus or residue. In this embodiment, the concentration of the yellow pigment is calculated based on the signal ratio Gp/Bp between the Bp image signal and the Gp image signal.

Figure 9:
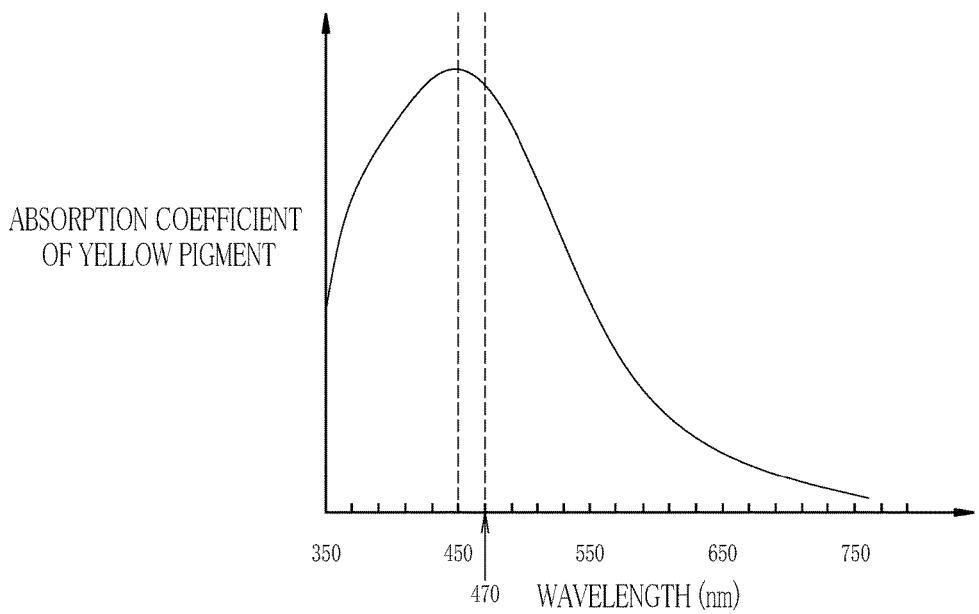
FIG. 9 is a graph illustrating an absorption coefficient of yellow pigment.

As shown in FIG. 9, the wavelength band of 450±10 nm of the first blue light BS corresponding to the Bp image signal includes the absorption peak wavelength at which the absorption coefficient of the yellow pigment is the highest, and therefore the light absorption amount easily changes in accordance with the concentration of the yellow pigment. Further, as shown in FIG. 10, the wavelength band of 450±10 nm of the first blue light BS belongs to a blue wavelength band at which the absorption coefficient of hemoglobin is relatively high, and includes an isosbestic wavelength at which oxygenated hemoglobin (graph 76) and reduced hemoglobin (graph 78) have the same absorption coefficient. In contrast, at the wavelength band of 540±20 nm of the green narrowband light Gn corresponding to the Gp image signal, an absorption coefficient of the yellow pigment is relatively low (see FIG. 9), and an absorption coefficient of the hemoglobin is relatively high (see FIG. 10), and therefore, the light absorption amount easily changes in accordance with the blood volume. Consequently, the value of the signal ratio Gp/Bp does not change in accordance with the oxygen saturation level, but changes in accordance with the concentration of the yellow pigment and the blood volume.

The prescribed exposure amount calculator 73 calculates the prescribed exposure amount of the second blue light BL for the second preliminary imaging in accordance with the concentration of the yellow pigment calculated by the yellow pigment concentration calculator 72. Hereinbelow, the prescribed exposure amount is explained. The prescribed exposure amount means an exposure amount for preventing occurrence of errors in the measurement result of the oxygen saturation level by pretending that the observation target does not have the yellow pigment even if the observation target has the yellow pigment. Here, at the wavelength band of 470±10 nm of the second blue light BL for use in measurement of the oxygen saturation level, there is a large difference in the absorption coefficient between the oxygenated hemoglobin (graph 76) and the reduced hemoglobin (graph 78) (see FIG. 10), and since the light absorption amount changes in accordance with the oxygen saturation level of the hemoglobin, it becomes easier to deal with the information of the oxygen saturation level. In contrast, at the wavelength band of 470±10 nm of the second blue light BL, the absorption coefficient of the yellow pigment is relatively high (see FIG. 9), and the light absorption amount easily changes in accordance with the concentration of the yellow pigment, and therefore errors may occur in the measurement result of the oxygen saturation level due to the amount of the second blue light BL which is absorbed by the yellow pigment in some cases. Consequently, the prescribed exposure amount of the second blue light BL is specified such that the amount of the light which is absorbed by the yellow pigment is compensated even if the observation target has the yellow pigment, at the time of measuring the oxygen saturation level.

For example, the prescribed exposure amount calculator 73 increases the prescribed exposure amount of the second blue light BL for the second preliminary imaging so as to compensate the amount of the second blue light BL which is absorbed by the yellow pigment, as the concentration of the yellow pigment becomes higher.

The prescribed exposure amount of the second blue light BL for the second preliminary imaging calculated by the prescribed exposure amount calculator 73 is inputted to the control section 60. The control section 60 calculates a prescribed light emission amount of the second blue light BL for the second preliminary imaging and a prescribed exposure time of the image capturing sensor 36 for the second preliminary imaging in accordance with the prescribed exposure amount of the second blue light BL for the second preliminary imaging, so as to control the light emission amount and the exposure time in the second preliminary imaging. In the light source controller 23, the second preliminary light emission is performed in accordance with the prescribed light emission amount of the second blue light BL for the second preliminary imaging, distance information of the observation target, and the like. In the image capturing controller 42, the second preliminary image capturing is performed in accordance with the prescribed exposure time of the image capturing sensor 36 for the second preliminary imaging. Thereby, the second preliminary imaging is performed in accordance with the prescribed exposure amount of the second blue light BL for the second preliminary imaging. Incidentally, in this embodiment, the control section 60 increases the prescribed light emission amount of the second blue light BL for the second preliminary imaging, as the prescribed exposure amount of the second blue light BL for the second preliminary imaging becomes larger, so as to compensate the amount of the second blue light BL which is absorbed by the yellow pigment.

The arithmetic value calculator 74 calculates the arithmetic value by performing a specific calculation based on at least the Bq image signal among the Bq image signal, the Gq image signal, and the Rq image signal which have been obtained by performing the second preliminary imaging in accordance with the prescribed exposure amount of the second blue light BL for the second preliminary imaging. In this embodiment, the arithmetic value calculator 74 divides the Bq image signal by the Gq image signal to obtain the signal ratio Bq/Gq as the arithmetic value. Namely, the specific calculation is to calculate the ratio of the Bq image signal to the Gq image signal. The value of the signal ratio Bq/Gq does not change in accordance with the concentration of the yellow pigment, but changes in accordance with the oxygen saturation level and the blood volume.

The determination section 75 determines whether or not the arithmetic value calculated by the arithmetic value calculator 74 has become closer to an optimum value specified in advance. The optimum value is a value which is obtained when the observation target does not have the yellow pigment. In the case where the observation target does not have the yellow pigment, the observation target may have no or little yellow pigment. In this embodiment, the determination section 75 determines whether or not the signal ratio Bq/Gq has become closer to the optimum value. In the case where the signal ratio Bq/Gq has become closer to the optimum value, a difference value between the value of the signal ratio Bq/Gq and the optimum value becomes equal to or less than a specific threshold value, for example.

In the case where the determination section 75 determines whether or not the signal ratio Bq/Gq has become closer to the optimum value, the determination section 75 calculates a difference value between the value of the signal ratio Bq/Gq and the optimum value, and compares the difference value with the specific threshold value. As a result of the comparison, the determination section 75 determines that the signal ratio Bq/Gq has become closer to the optimum value when the difference value is equal to or less than the threshold value, and determines that the signal ratio Bq/Gq has not become closer to the optimum value yet when the difference value is more than the threshold value. In the case where it is determined that the signal ratio Bq/Gq has become closer to the optimum value, even if the observation target actually has the yellow pigment, it is possible to calculate the oxygen saturation level by pretending that the observation target does not have the yellow pigment, because the amount of the second blue light BL which is absorbed by the yellow pigment is compensated. Consequently, in the case where it is determined that the signal ratio Bq/Gq has become closer to the optimum value, it is possible to prevent the yellow pigment from causing errors at the time of calculating the oxygen saturation level.

The determination result from the determination section 75 is inputted to the control section 60. As shown in FIG. 11, the control section 60 determines whether or not to perform the main imaging based on the determination result from the determination section 75. Specifically, in the case where it is determined that the signal ratio Bq/Gq has not become closer to the optimum value yet (NO in FIG. 11), the control section 60 performs the first preliminary imaging again, such that the concentration of the yellow pigment and the prescribed exposure amount are calculated again.

In contrast, in the case where it is determined that the signal ratio Bq/Gq has become closer to the optimum value (YES. in FIG. 11), the control section 60 decides to perform the main imaging in accordance with the prescribed exposure amount of the second blue light BL for the second preliminary imaging. In response to the decision, the control section 60 completes the preliminary imaging mode, and switches the currently-set mode to the main imaging mode. In the case where the currently-set mode is switched to the main imaging mode, the control section 60 calculates the prescribed exposure amount of the second blue light BL for the main imaging in accordance with the prescribed exposure amount of the second blue light BL for the second preliminary imaging. Then, the control section 60 calculates the prescribed light emission amount of the second blue light BL for the main imaging and the prescribed exposure time of the image capturing sensor 36 for the main imaging in accordance with the prescribed exposure amount of the second blue light BL for the main imaging, and thereby controls the light emission amount and the exposure time in the main imaging. In the light source controller 23, the first main light emission and the second main light emission are performed in accordance with the prescribed light emission amount of the second blue light BL for the main imaging, the distance information of the observation target, and the like. In the image capturing controller 42, the first main image capturing and the second main image capturing are performed in accordance with the prescribed exposure time of the image capturing sensor 36 for the main imaging.

The oxygen saturation image generator 64 calculates the oxygen saturation level of the observation target with use of the correlation between the oxygen saturation level and the B1, G2, and R2 image signals among the image signals obtained by performing the main imaging in the main imaging mode. Then, the oxygen saturation image generator 64 generates the oxygen saturation image in which the calculated oxygen saturation level is visualized using pseudo color or the like.

Figure 12:
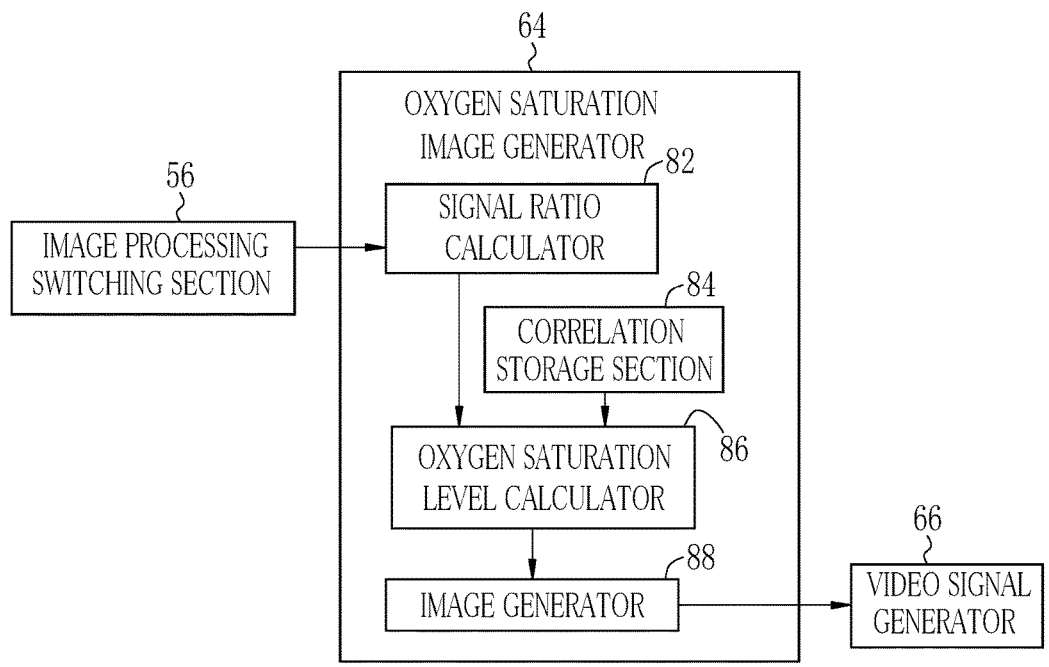
FIG. 12 is a block diagram illustrating functions of an oxygen saturation image generator.

As shown in FIG. 12, the oxygen saturation image generator 64 includes a signal ratio calculator 82, a correlation storage section 84, an oxygen saturation level calculator 86, and an image generator 88.

The signal ratio calculator 82 calculates the signal ratio for use in calculation of the oxygen saturation level in the oxygen saturation level calculator 86 based on the image signal received from the image processing switching section 56. Specifically, the signal ratio calculator 82 calculates the signal ratio B1/G2 between the B1 image signal and the G2 image signal, and the signal ratio R2/G2 between the R2 image signal and the G2 image signal, for each pixel.

Figure 13:
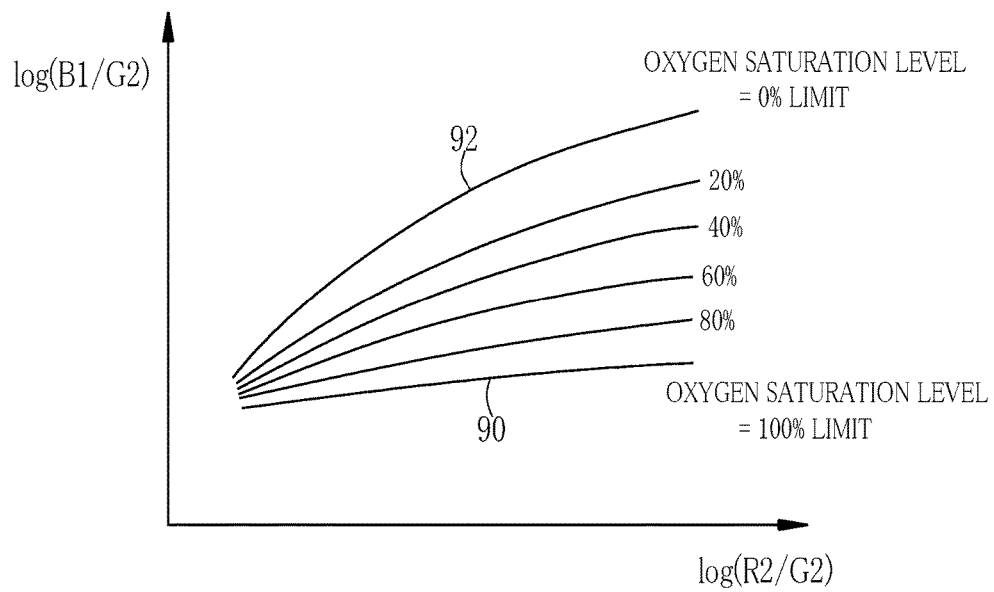
FIG. 13 illustrates a correlation between a signal ratio and an oxygen saturation level.

The correlation storage section 84 stores the correlation between the oxygen saturation level and each of the signal ratios calculated by the signal ratio calculator 82 in a storage such as LUT (Look Up Table). In the case where the correlation is represented in the two-dimensional space consisting of a longitudinal axis Log (B1/G2) and a horizontal axis Log (R2/G2), as shown in FIG. 13, an isocline obtained by connecting portions having the same oxygen saturation level extends approximately along the horizontal axis in the two-dimensional space. Further, as the oxygen saturation level becomes higher, the isocline is located at a lower position with respect to the longitudinal axis. For example, an isocline 90 having the oxygen saturation level of 100% is located at a lower position with respect to an isocline 92 having the oxygen saturation level of 0%. Incidentally, the position and the shape of the isocline in the two-dimensional space are obtained in advance by physical simulation of light scattering.

The above correlation is closely associated with the light absorption characteristics and light-scattering properties of the oxygenated hemoglobin (graph 76 in FIG. 10) and the reduced hemoglobin (graph 78 in FIG. 10). The signal ratio B1/G2 highly depends on not only the oxygen saturation level but also the blood volume. Accordingly, in addition to the signal ratio B1/G2, the signal ratio R2/G2, which changes mainly depending on the blood volume, is used, so as to calculate the oxygen saturation level from which an influence by the blood volume is removed.

The oxygen saturation level calculator 86 refers to the correlation stored in the correlation storage section 84, and calculates the oxygen saturation level corresponding to each of the signal ratio B1/G2 and the signal ratio R2/G2 for each pixel. In the oxygen saturation level calculator 86, the signal ratio B1/G2 in which the amount of the second blue light BL which is absorbed by the yellow pigment is compensated as described above is used, and therefore even if the observation target has the yellow pigment, it is possible to calculate the oxygen saturation level with a high degree of accuracy.

Incidentally, when the calculated oxygen saturation is located at a lower position with respect to the upper limit isocline 90, the oxygen saturation level calculator 86 concludes that the oxygen saturation level is 100%, and when the calculated oxygen saturation is located at an upper position with respect to the lower limit isocline 92, the oxygen saturation level calculator 86 concludes that the oxygen saturation level is 0%. In addition, in the case where a point corresponding to the signal ratios B1/G2 and R2/G2 deviates from a region between the upper limit isocline 90 and the lower limit isocline 92, the fact that a degree of reliability of the oxygen saturation level in the pixel is low may be displayed on the monitor 18, or the oxygen saturation level may not be calculated.

The image generator 88 generates the oxygen saturation image in which the oxygen saturation level of the observation target is represented based on the oxygen saturation level calculated by the oxygen saturation level calculator 86 and the image signal obtained by performing the main imaging. Specifically, the image generator 88 performs gainmultiplication for pseudo coloring for each pixel in accordance with the oxygen saturation level for the B2 image signal, the G2 image signal, and the R2 image signal, so as to generate the RGB image data. The generated RGB image data is inputted to the video signal generator 66. The RGB image data corresponds to the oxygen saturation image. In the oxygen saturation image, a high-oxygen region (region having an oxygen saturation level of not less than 60% to not more than 100%) is expressed in the same color as the normal image. On the other hand, a low-oxygen region where the oxygen saturation level is less than a specific value (region having an oxygen saturation level of not less than 0% to less than 60%) is expressed in a different color from the normal image, i.e., pseudo color.

The video signal generator 66 converts the image data of the normal image from the normal image generator 58 or the image data of the oxygen saturation image from the oxygen saturation image generator 64 into a video signal which is capable of being displayed in full color on the monitor 18. The video signal subjected to the conversion is inputted to the monitor 18. Thereby, the normal image or the oxygen saturation image is displayed on the monitor 18.

Figure 14:
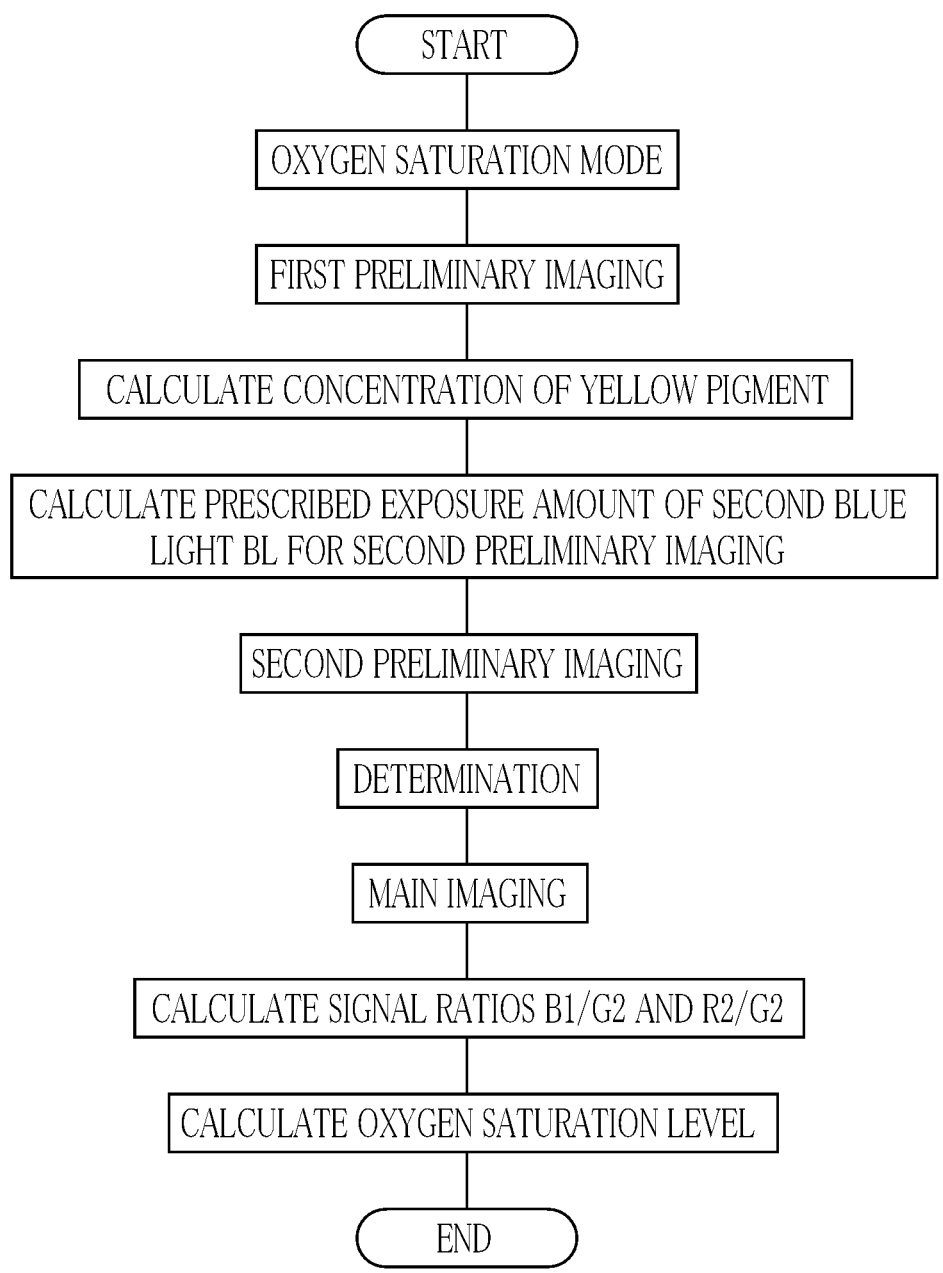
FIG. 14 is a flowchart illustrating functions of the endoscope system according to the first embodiment.

Next, a procedure of processing using the endoscope system 10 according to the present invention will be described with reference to the flowchart in FIG. 14. In the normal mode, when the mode switching section 12f is operated, the currently-set mode is switched to the oxygen saturation mode. In the case where the currently-set mode is switched to the oxygen saturation mode, cleaning fluid is sprayed toward the observation target from the distal end portion 12d of the endoscope 12, and the control section 60 executes the preliminary imaging mode.

Figure 15:
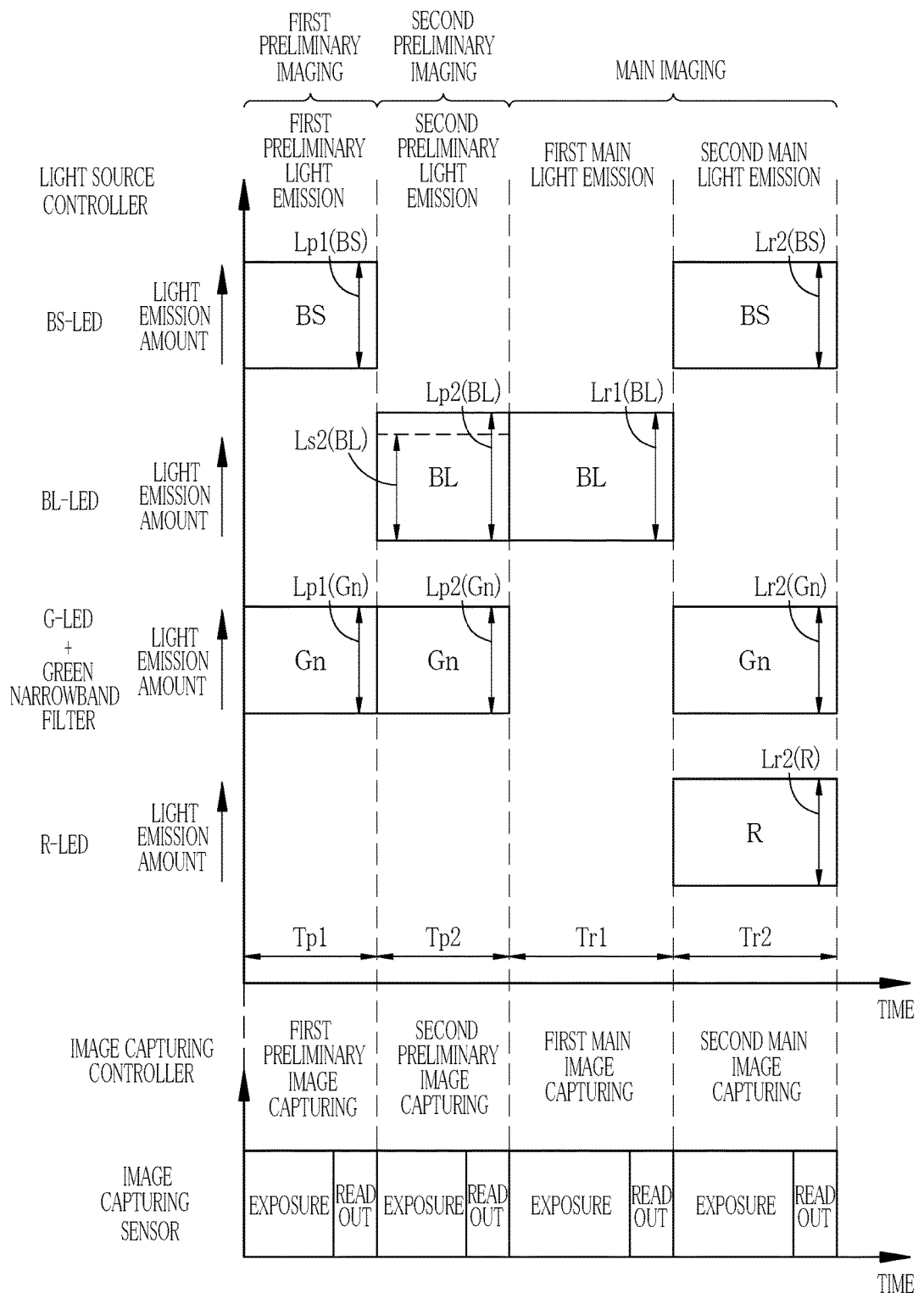
FIG. 15 illustrates light emission control and image capturing control in accordance with a prescribed exposure amount of second blue light in the oxygen saturation mode.

When the preliminary imaging mode is executed, at first, the first preliminary imaging is performed. As shown in FIG. 15, in the first preliminary imaging, the control section 60 controls the light source controller 23, such that the first preliminary light emission in which the first blue light BS and the green narrowband light Gn are emitted at the same time is performed, and the control section 60 controls the image capturing controller 42, such that the first preliminary image capturing in which an image of the observation target illuminated with the first blue light BS and the green narrowband light Gn is captured is performed. Thereby, in the first preliminary imaging, the Bp image signal, the Gp image signal, and the Rp image signal are obtained. Incidentally, there is performed the first preliminary light emission, in which the first blue light BS at a prescribed light emission amount Lp1 (BS) of the first blue light BS for the first preliminary imaging, and the green narrowband light Gn at a prescribed light emission amount Lp1 (Gn) of the green narrowband light Gn for the first preliminary imaging are emitted in accordance with the prescribed exposure amount for the first preliminary imaging which has been specified in advance. Further, the first preliminary image capturing is performed in a prescribed exposure time Tp1 of the image capturing sensor 36 for the first preliminary imaging.

The yellow pigment concentration calculator 72 calculates the concentration of the yellow pigment based on the signal ratio Gp/Bp between the Bp image signal and the Gp image signal among the image signals obtained by performing the first preliminary imaging. The prescribed exposure amount calculator 73 calculates the prescribed exposure amount of the second blue light BL for the second preliminary imaging based on the calculated concentration of the yellow pigment. Then, in accordance with the prescribed exposure amount of the second blue light BL for the second preliminary imaging, a prescribed light emission amount Lp2 (BL) of the second blue light BL for the second preliminary imaging, a prescribed light emission amount Lp2 (Gn) of the green narrowband light Gn for the second preliminary imaging, and a prescribed exposure time Tp2 of the image capturing sensor 36 for the second preliminary imaging are calculated. Note that, in this embodiment, the prescribed light emission amount Lp2 (BL) of the second blue light BL for the second preliminary imaging in the case where the observation target has the yellow pigment is calculated. The prescribed light emission amount Lp2 (BL) of the second blue light BL for the second preliminary imaging is made larger than a prescribed light emission amount Ls2 (BL) of the second blue light BL for the second preliminary imaging which is calculated in the case where the observation target does not have the yellow pigment (see FIG. 15), and thereby it is possible to compensate the amount of the second blue light BL which is absorbed by the yellow pigment.

Next, the second preliminary imaging is performed. In the second preliminary imaging, the control section 60 controls the light source controller 23, such that the second preliminary light emission in which the second blue light BL and the green narrowband light Gn are emitted at the same time in accordance with the prescribed light emission amounts Lp2 (BL) and the Lp2 (Gn) for the second preliminary imaging is performed. Concurrently, the control section 60 controls the image capturing controller 42, such that there is performed the second preliminary image capturing, in which an image of the observation target illuminated with the second blue light BL and the green narrowband light Gn is captured in accordance with the prescribed exposure time Tp2 for the second preliminary imaging. Thereby, in the second preliminary imaging, the Bq image signal, the Gq image signal, and the Rq image signal are obtained.

The arithmetic value calculator 74 calculates the signal ratio Bq/Gq between the Bq image signal and the Gq image signal among the image signals obtained by performing the second preliminary imaging as the arithmetic value. The determination section 75 determines whether or not the signal ratio Bq/Gq has become closer to the optimum value. As a result of the determination, in the case where it is determined that the signal ratio Bq/Gq has become closer to the optimum value, it is decided to perform the main imaging in accordance with the prescribed exposure amount of the second blue light BL for the second preliminary imaging, and the preliminary imaging mode is completed, and then the currently-set mode is switched to the main imaging mode.

When the currently-set mode is switched to the main imaging mode, the prescribed exposure amount of the second blue light BL for the main imaging is calculated in accordance with the prescribed exposure amount of the second blue light BL for the second preliminary imaging. Then, in accordance with the prescribed exposure amount of the second blue light BL for the main imaging, a prescribed light emission amount Lr1 (BL) of the second blue light BL for the main imaging in the first main light emission is calculated, and a prescribed exposure time Tr1 of the image capturing sensor 36 for the main imaging in the first main image capturing is calculated. Further, a prescribed light emission amount Lr2 (BS) of the first blue light BS for the main imaging in the second main light emission, a prescribed light emission amount Lr2 (Gn) of the green narrowband light Gn for the main imaging, and a prescribed light emission amount Lr2 (R) of the red light R for the main imaging are calculated, and a prescribed exposure time Tr2 of the image capturing sensor 36 for the main imaging in the second main image capturing is calculated.

In the main imaging, one set of the first main light emission and the first main image capturing and one set of the second main light emission and the second main image capturing are alternately performed. Thereby, in the case where the first main light emission and the first main image capturing are performed, the B1 image signal, the G1 image signal, and the R1 image signal are obtained. Further, in the case where the second main light emission and the second main image capturing are performed, the B2 image signal, the G2 image signal, and the R2 image signal are obtained. Incidentally, in the main imaging, the prescribed light emission amount Lr1 (BL) of the second blue light BL for the main imaging in the first main light emission is made larger, and thereby it is possible to compensate the amount of the second blue light BL which is absorbed by the yellow pigment.

The signal ratio calculator 82 calculates the signal ratio B1/G2 between the B1 image signal and the G2 image signal, and the signal ratio R2/G2 between the R2 image signal and the G2 image signal, among the image signals obtained by performing the main imaging. The oxygen saturation level calculator 86 calculates the oxygen saturation level corresponding to each of the signal ratio B1/G2 and the signal ratio R2/G2 with reference to the correlation stored in the correlation storage section 84. The image generator 88 generates the oxygen saturation image based on the calculated oxygen saturation level and the image signal obtained by performing the main imaging.

As described above, according to the endoscope system 10 of the present invention, in the first preliminary imaging, the concentration of the yellow pigment is calculated based on the image signal obtained by capturing an image of the observation target illuminated with the first blue light BS, and the prescribed exposure amount of the second blue light BL in the second preliminary imaging is calculated based on the concentration of the yellow pigment. In the second preliminary imaging, based on the image signal obtained by capturing an image of the observation target illuminated with the second blue light BL in accordance with the above prescribed exposure amount, the specific calculation is performed so as to calculate the arithmetic value, and it is determined whether or not the arithmetic value has become closer to the optimum value. Even in the case where the second blue light BL is absorbed by the yellow pigment contained in the observation target, the oxygen saturation level can be calculated with a high degree of accuracy by performing the first preliminary imaging and the second preliminary imaging as described above.

Further, in the endoscope system 10 of the present invention, the prescribed exposure time Tp1 of the image capturing sensor 36 for the first preliminary imaging is made shorter than the prescribed exposure time Tr1 of the image capturing sensor 36 for the main imaging, and the prescribed exposure time Tp2 of the image capturing sensor 36 for the second preliminary imaging is made shorter than the prescribed exposure time Tr2 of the image capturing sensor 36 for the main imaging (see FIG. 15). Thereby, the time lag until the oxygen saturation image is obtained becomes short, and thereby it becomes possible to make a diagnosis using the oxygen saturation image in a rapid manner.

Note that, in the above embodiment, the first preliminary imaging and the second preliminary imaging are performed at the timing when the currently-set mode is switched to the oxygen saturation mode. However, the first preliminary imaging and the second preliminary imaging may be performed at another timing. For example, in the case where instructions for acquiring a still image are outputted in response to the operation of the still-image acquisition instructing section 12g, the first preliminary imaging and the second preliminary imaging may be performed. In the case where the still image of the observation target is acquired, it is highly possible that a doctor performs detailed examination of the observation target, and therefore it is preferable that the oxygen saturation level is correctly represented in the oxygen saturation image acquired as the still image. Therefore, in the case where the instructions for acquiring the still image are outputted, it is possible to provide a doctor with an oxygen saturation image in which the oxygen saturation level is correctly reflected as the still image by performing the first preliminary imaging and the second preliminary imaging.

Figures 16, 17:
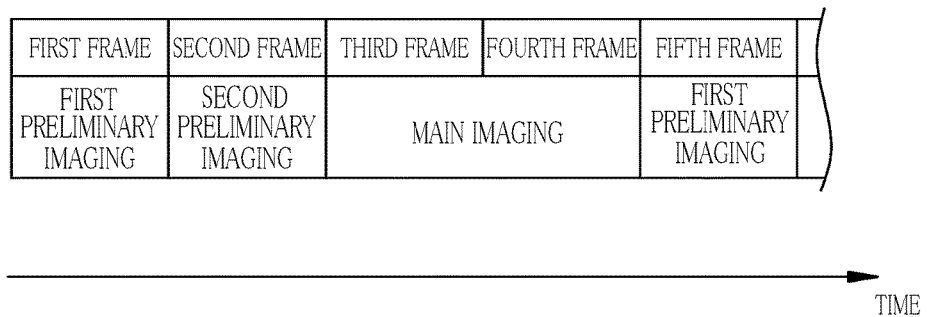
FIG. 16 illustrates first preliminary imaging, second preliminary imaging, and the main imaging while a moving image is displayed.
FIG. 17 illustrates signal readout by a thin-out reading method.

Further, while the moving image of the observation target based on the oxygen saturation images is displayed, the first preliminary imaging and the second preliminary imaging may be performed. For example, as shown in FIG. 16, while the moving image is displayed, the first preliminary imaging is performed in the first frame, the second preliminary imaging is performed in the second frame, the main imaging is performed in the third frame and the fourth frame, and one set of the first preliminary imaging, the second preliminary imaging, and the main imaging is sequentially repeated in the same manner in the fifth frame and the subsequent frames. In the case where the images constituting the moving image are obtained, at least the image signal obtained in the frame in which the main imaging is performed is used among the frames while the moving image is displayed. Thereby, in the case where the moving image is displayed, it is possible to calculate the oxygen saturation level with a high degree of accuracy.

Furthermore, while the moving image is displayed, the present invention is not limited to the case where one set of the first preliminary imaging, the second preliminary imaging, and the main imaging is sequentially repeated. For example, the frame in which the first preliminary imaging and second preliminary imaging are performed may be intermittently provided each time a certain period of time elapses. Thereby, it is possible to prevent decrease in the frame rate of the moving image.

Moreover, in the case where the moving amount of the observation target is detected based on the image obtained in the frame in which the main imaging is performed and the detected moving amount is equal to or less than a specific value, a frame in which the first preliminary imaging and the second preliminary imaging are performed may be provided. In the case where the moving amount is equal to or less than the specific value, it is possible that the movement of the endoscope is stopped to perform the detailed examination of the observation target. Accordingly, the frame in which the first preliminary imaging and the second preliminary imaging are performed is provided, and thereby the oxygen saturation image in which the oxygen saturation level is correctly represented can be provided. On the contrary, in the case where the moving amount exceeds the specific value, it is possible that the endoscope is moved by a large amount due to the screening or the like. Therefore, the frame in which the first preliminary imaging and the second preliminary imaging are performed is not provided, and thereby the burden on the processor device 16 for the processing can be decreased.

Note that, in above embodiment, at the time of acquiring the oxygen saturation image, only the image signal obtained by performing the main imaging is used. However, in addition to the image signal obtained by performing the main imaging, the image signals obtained by performing the first preliminary imaging and the second preliminary imaging may be used. In this regard, since the illumination time in the first preliminary imaging and the second preliminary imaging is shorter than the illumination time in the main imaging, the prescribed exposure amount in the first preliminary imaging and the second preliminary imaging is smaller than the prescribed exposure in the main imaging. Accordingly, in the case where an image is generated based on the image signal obtained by performing the first preliminary imaging and the second preliminary imaging, it is preferable that the image signal is subjected to signal processing such as amplification of the luminance value, for the purpose of compensating the shortage of the prescribed exposure amount. Thereby, for example, in the case where the moving image is displayed, it is possible to display the moving image with high image quality in which the frame rate is high and the flickering between the images is suppressed.

Note that, although the image capturing controller 42 controls such that the signals are read out by the all-pixel reading method for the image capturing sensor 36 in the above embodiment, the signals may be read out by the thin-out reading method. For example, as shown in FIG. 17, in the case where the first preliminary imaging and the second preliminary imaging are performed, the signals may be read out from each of the B pixels and the G pixels. In this case, the image capturing controller 42 controls such that the signals are read out from the B pixels and the G pixels in an even number of pixel rows among an even number (i.e., 0, 2, 4, . . . , N−1) of pixel rows and an odd number (i.e., 1, 3, 5, . . . , N) of pixel rows. In contrast, the image capturing controller 42 controls such that the signals are read out from only the G pixels and the signals are not read out from the R pixels in an odd number of pixel rows. Thereby, in the first preliminary imaging, the Bp image signal and the Gp image signal for use in calculation of the concentration of the yellow pigment are obtained. Further, in the second preliminary imaging, the Bq image signal and the Gq image signal for use in calculation of the arithmetic value are obtained. Since the signals are readout from the B pixels and the G pixels without reading out the signals from the R pixels as described above, the time required for reading out the signals in the first preliminary imaging and the second preliminary imaging is shortened.

Further, in the case where the signals are read out by the thin-out reading method, the signals may be read out on a pixel row by pixel row basis from an even number of pixel rows, and the signals may not be read out from an odd number of pixel rows. Thereby, since the signals are readout from only half of the pixels out of all the pixels, the time required for reading out the signals is cut approximately in half. Note that, in the case where the first preliminary imaging and the second preliminary imaging are performed, the signals may not be read out from the pixels other than the B pixels (i.e., specific pixels) out of the B pixels, the G pixels, and the R pixels, and the signals may be read out from the B pixels.

Incidentally, in the above embodiment, the green narrowband light Gn is generated by restricting the wavelength band of the green light G from the G-LED 20c by the green narrowband filter 21. Alternatively, the green narrowband light Gn may be generated by restricting the wavelength band of the broadband light (white light) from the broadband light source by the green narrowband filter 21. According to the present invention, as described above, the broadband light includes not only the green light G at the wavelength band in the range of 500 nm to 600 nm but also white light and the like. Note that, the broadband light source is a semiconductor light source such as white LED or a xenon lamp.

Figure 18:
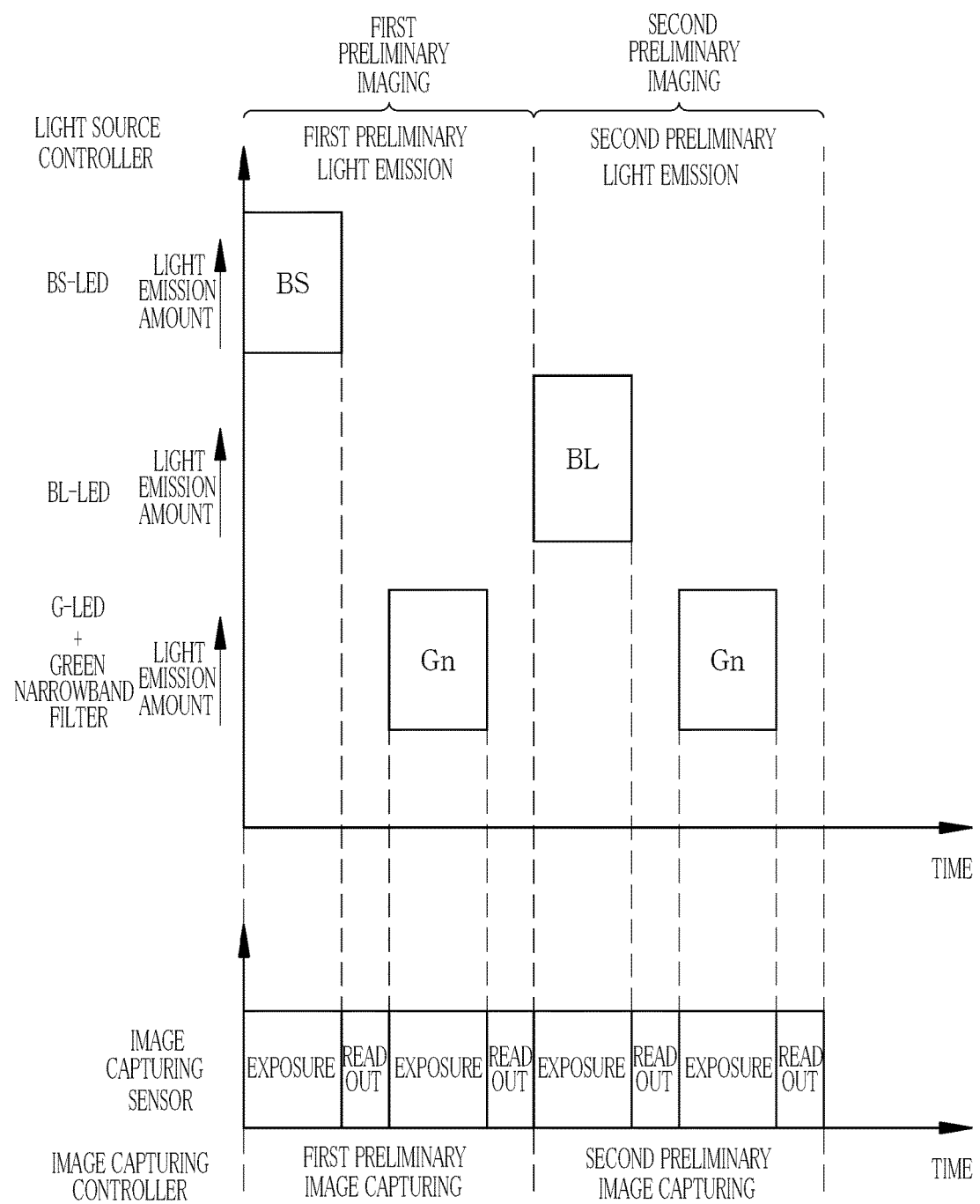
FIG. 18 illustrates sequential light emission in the first preliminary imaging and the second preliminary imaging.

Further, according to the above embodiment, the control section 60 emits the first blue light BS and the green narrowband light Gn at the same time at the time of performing the first preliminary imaging, and emits the second blue light BL and the green narrowband light Gn at the same time at the time of performing the second preliminary imaging. Alternatively, the first blue light BS and the green narrowband light Gn may be emitted in a sequential manner at the time of performing the first preliminary imaging, and the second blue light BL and the green narrowband light Gn may be emitted in a sequential manner at the time of performing the second preliminary imaging. For example, as shown in FIG. 18, the control section 60 turns on each of the LEDs during the exposure time by the image capturing sensor 36, and turns off each of the LEDs during the signal readout time by the image capturing sensor 36. The exposure time of each kind of light in the case of the sequential light emission is approximately half of that in the case of the simultaneous light emission, and therefore the light emission amount of each kind of light is doubled. Thereby, in comparison with the case of the simultaneous light emission, since a period for which the BS-LED 20a, the BL-LED 20b, and the G-LED 20c are turned off and the light source device 14 is cooled down is provided, heat generation of the light source device 14 can be suppressed. Note that, in the case where the exposure amount in the first and second preliminary imaging may be relatively small, such as the case where the image signals obtained by performing the first and second preliminary imaging are not used at the time of acquiring the oxygen saturation image, an increase in the driving current of the light source device 14 is suppressed by avoiding the increase in the light emission amount of each kind of light, and thereby the heat generation can be further suppressed.

Figure 19:
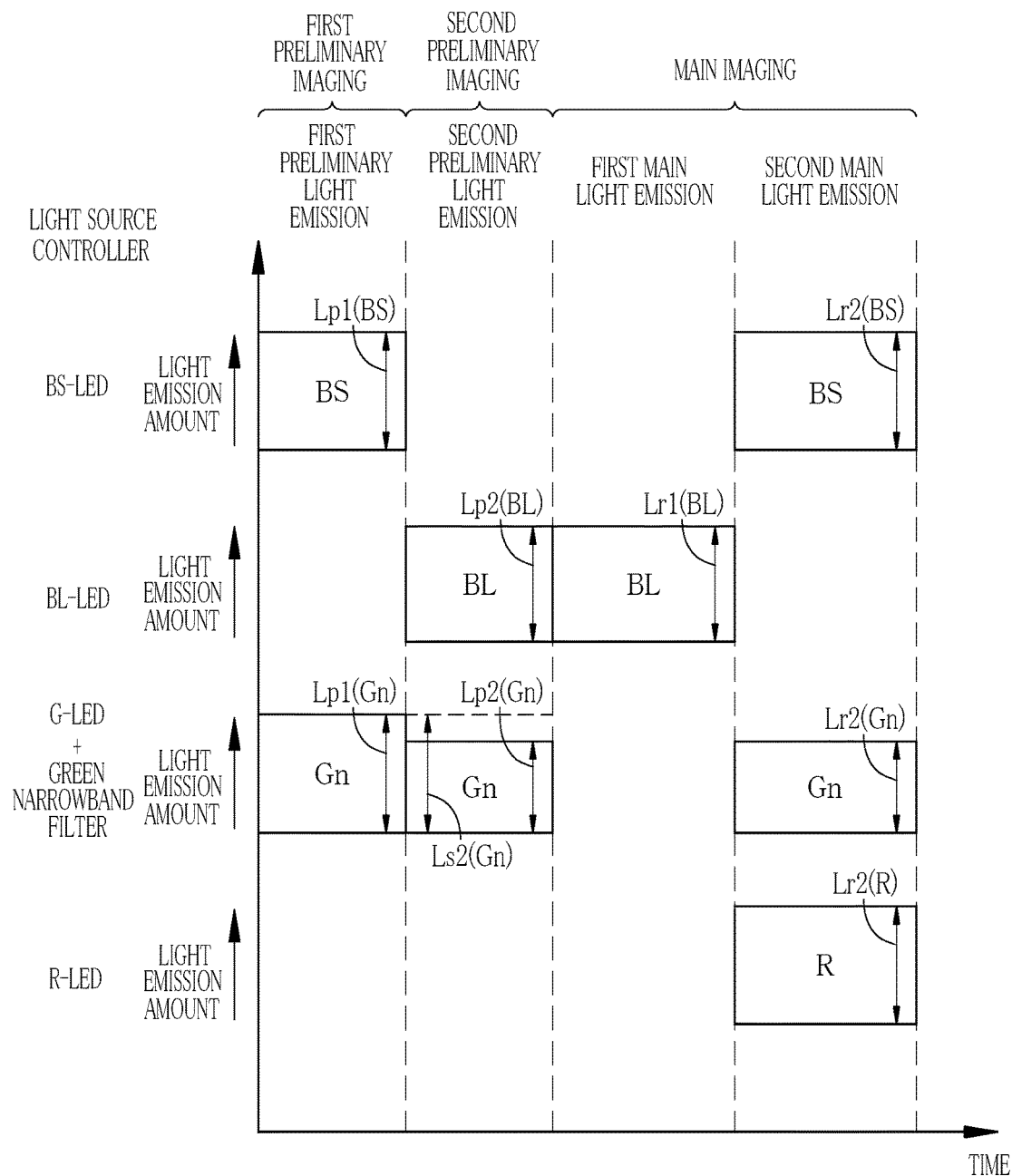
FIG. 19 illustrates the light emission control and the image capturing control in accordance with a prescribed exposure amount of green narrowband light in the oxygen saturation mode.

In the above embodiment, the prescribed exposure amount calculator 73 calculates the prescribed exposure amount of the second blue light BL for the second preliminary imaging based on the concentration of the yellow pigment calculated by the yellow pigment concentration calculator 72. Alternatively, the prescribed exposure amount of the green narrowband light Gn for the second preliminary imaging may be calculated. In the case of calculating the prescribed exposure amount of the green narrowband light Gn for the second preliminary imaging, the prescribed exposure amount calculator 73 decreases the prescribed exposure amount of the green narrowband light Gn for the second preliminary imaging as the concentration of the yellow pigment is increased. In this case, the control section 60 calculates the prescribed light emission amount Lp2 (Gn) of the green narrowband light Gn for the second preliminary imaging as shown in FIG. 19. The prescribed light emission amount Lp2 (Gn) of the green narrowband light Gn for the second preliminary imaging is smaller than the prescribed light emission amount Ls2 (Gn) of the green narrowband light Gn for the second preliminary imaging obtained in the case where the observation target does not have the yellow pigment. Thereby, the value of the signal ratio Bq/Gq calculated by the arithmetic value calculator 74 is the same between the case where the observation target has the yellow pigment and the case where the does not have the yellow pigment. Consequently, the determination is performed correctly by the determination section 75, and the oxygen saturation level can be calculated with a high degree of accuracy.

Moreover, as the concentration of the yellow pigment becomes higher, the prescribed exposure amount calculator 73 may increase the prescribed exposure amount of the second blue light BL for the second preliminary imaging and decrease the prescribed exposure amount of the green narrowband light Gn for the second preliminary imaging. Accordingly, in comparison with the case where only the prescribed exposure amount of the second blue light BL for the second preliminary imaging is calculated, the value of current for driving the BL-LED 20b which emits the second blue light BL becomes smaller, and thereby heat generation of the light source device 14 can be suppressed. Further, in comparison with the case where only the prescribed exposure amount of the green narrowband light Gn for the second preliminary imaging is calculated, it is possible to suppress decrease in brightness in total which occurs in accordance with decrease in the prescribed light emission amount of the green narrowband light Gn.

Note that, in the above embodiment, the prescribed exposure amount calculator 73 calculates the prescribed exposure amount for the second preliminary imaging based on the concentration of the yellow pigment calculated by the yellow pigment concentration calculator 72. The prescribed exposure amount calculator 73 may calculate the prescribed exposure amount based on the luminance value of the pixel in addition to the concentration of the yellow pigment. The luminance value has gradation distribution in the range of 0 to 255. A so-called white defect occurs in the pixel in which the luminance value is a saturation value (i.e., 255), and the visibility of the observation target is decreased. Therefore, for example, the yellow pigment concentration calculator 72 averages the luminance values of the pixels based on the image signals obtained by performing the first preliminary imaging so as to calculate an average luminance value, and calculates the prescribed exposure amount for the second preliminary imaging such that the difference value between the average luminance value and the saturation value (i.e., 255) is equal to or more than the specific value. Since the main imaging is performed in accordance with the prescribed exposure amount for the second preliminary imaging calculated as described above, it is possible to prevent occurrence of the white defect and observe the observation target with high visibility.

Second Embodiment

According to a second embodiment, instead of the LEDs of four colors 20a to 20d described in the above first embodiment, the broadband light source such as the xenon lamp and a rotation filter are used, so as to illuminate the observation target. Additionally, an image of the observation target is captured by a monochrome image capturing sensor instead of the color image capturing sensor 36. The other features of the second embodiment are the same as those of the first embodiment.

Figure 20:
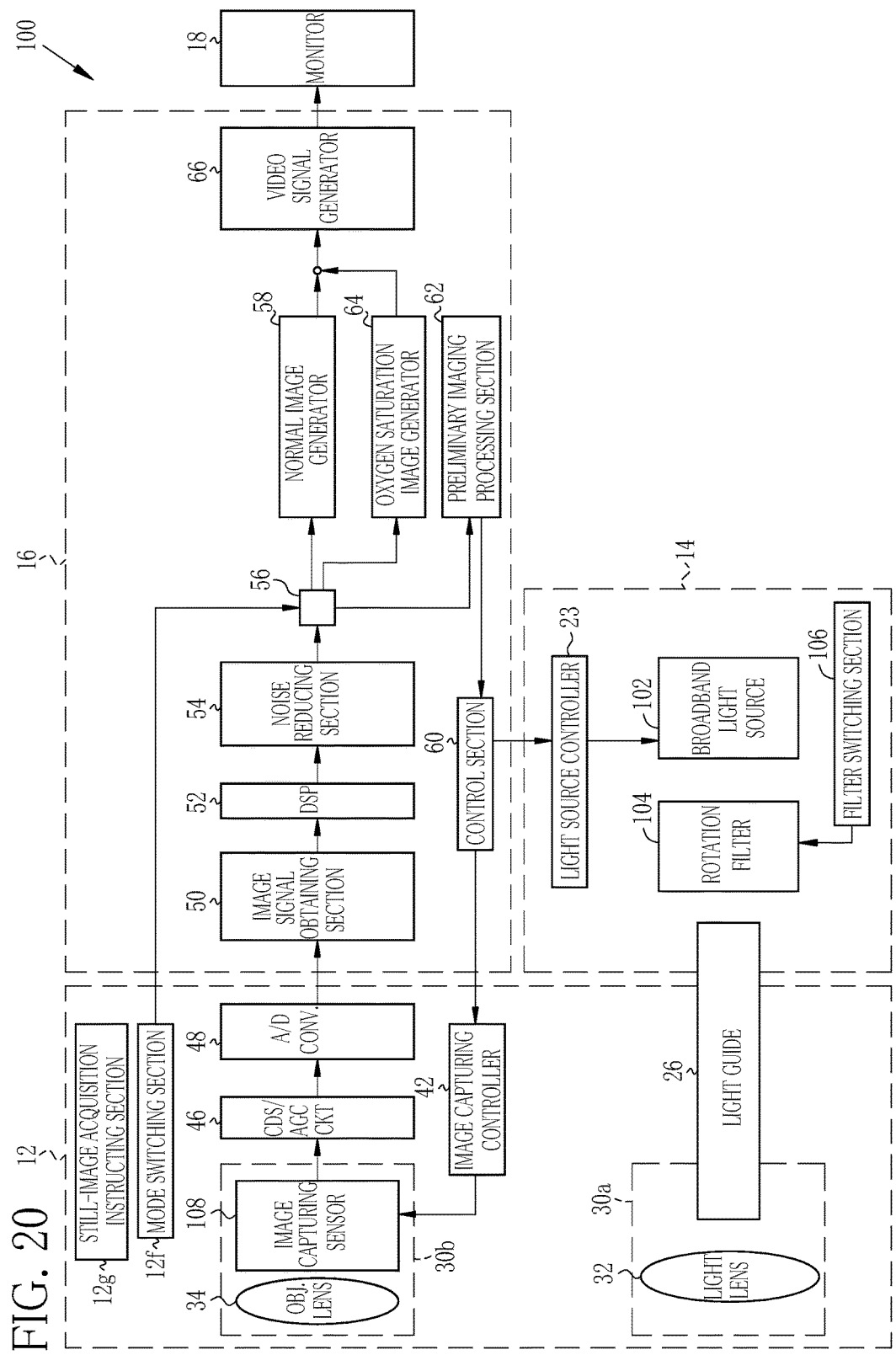
FIG. 20 is a block diagram illustrating functions of an endoscope system according to a second embodiment of the present invention.

As shown in FIG. 20, in an endoscope system 100, the light source device 14 includes a broadband light source 102, a rotation filter 104, and a filter switching section 106, instead of each of the LEDs 20a to 20d of the first embodiment. Additionally, the image capturing optical system 30b includes a monochrome image capturing sensor 108 having no color filters, instead of the color image capturing sensor 36.

The broadband light source 102 is a white LED, a xenon lamp, or the like, and emits white light at the wavelength band ranging from blue to red. The rotation filter 104 includes an inner filter 110, an intermediate filter 111, and an outer filter 112 (see FIG. 21) in this order from inside to outside.

The filter switching section 106 is electrically connected to the light source controller 23, and moves the rotation filter 104 in the radial direction depending on each mode controlled by the light source controller 23. In the case where the normal mode is set by the mode switching section 12f, the filter switching section 106 inserts the inner filter 110 of the rotation filter 104 to a light path of the white light.

In contrast, in the case where the oxygen saturation mode is set, the filter switching section 106 inserts the intermediate filter 111 or the outer filter 112 to the light path of the white light in accordance with the timing when each of the first preliminary imaging, the second preliminary imaging, and the main imaging is performed. Specifically, the filter switching section 106 inserts the intermediate filter 111 of the rotation filter 104 to the light path of the white light in the first preliminary imaging and the second preliminary imaging, and inserts the outer filter 112 of the rotation filter 104 to the light path of the white light in the main imaging.

Figure 21:
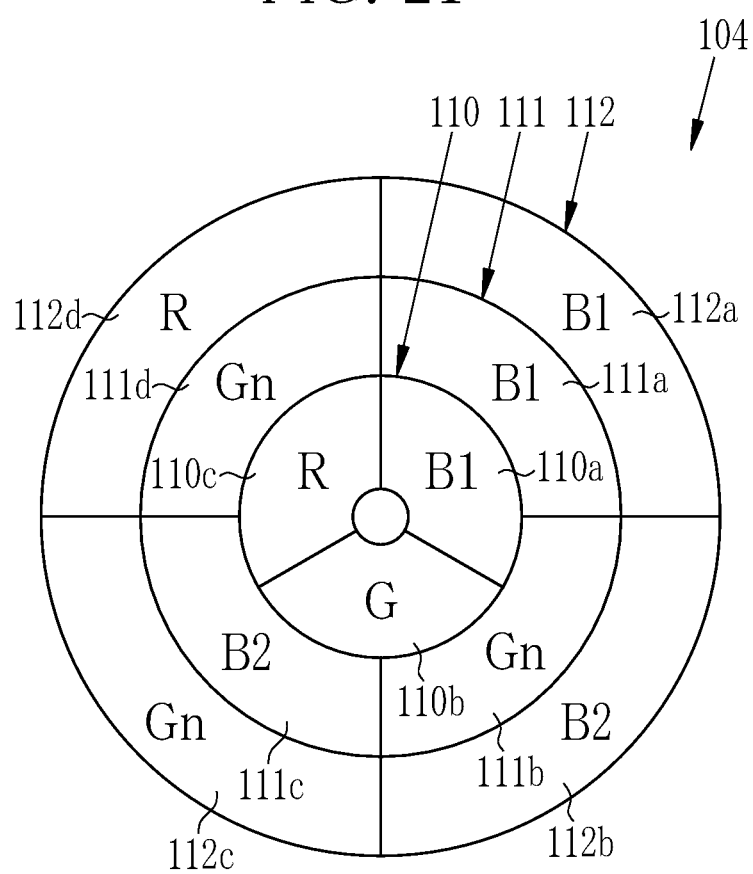
FIG. 21 is a plan view of a rotation filter.

As shown in FIG. 21, the inner filter 110 is provided with a B1 filter 110a through which the first blue light BS contained in the white light is transmitted, a G filter 110b through which the green light G contained in the white light is transmitted, and an R filter 110c through which the red light R contained in the white light is transmitted, arranged along the circumferential direction. Consequently, in the normal mode, upon rotation of the rotation filter 104, the first blue light BS, the green light G, and the red light R are sequentially irradiated toward the observation target.

The intermediate filter 111 is provided with a B1 filter 111a through which the first blue light BS contained in the white light is transmitted, a Gn filter 111b through which the green narrowband light Gn contained in the white light is transmitted, and a B2 filter 111c and a Gn filter 111d through which the second blue light BL contained in the white light is transmitted, arranged along the circumferential direction. Consequently, in the oxygen saturation mode, upon rotation of the rotation filter 104 in a state that the intermediate filter 111 is inserted to the light path of the white light, the first blue light BS, the green narrowband light Gn, the second blue light BL, and the green narrowband light Gn are sequentially irradiated toward the observation target. Thereby, the first preliminary imaging and the second preliminary imaging are performed.

The outer filter 112 is provided with a B1 filter 112a through which the first blue light BS contained in the white light is transmitted, a B2 filter 112b through which the second blue light BL contained in the white light is transmitted, a Gn filter 112c through which the green narrowband light Gn contained in the white light is transmitted, and a R filter 112d through which the red light R contained in the white light is transmitted, arranged along the circumferential direction. Consequently, in the oxygen saturation mode, upon rotation of the rotation filter 104 in a state that the outer filter 112 is inserted to the light path of the white light, the first blue light BS, the second blue light BL, the green narrowband light Gn, and the red light R are sequentially irradiated toward the observation target. Thereby, the main imaging is performed.

In the endoscope system 100, in the case of the normal mode, each time the observation target is illuminated with the first blue light BS, the green light G, and the red light R, an image of the observation target is captured by the monochrome image capturing sensor 108. Thereby, the Bc image signal, the Gc image signal, and the Rc image signal are obtained. Then, based on the image signals of three colors, the normal image is generated in the same manner as that of the above first embodiment.

In contrast, in the case of the oxygen saturation mode, in the first preliminary imaging, an image of the observation target is captured by the monochrome image capturing sensor 108 each time the observation target is illuminated with the first blue light BS and the green narrowband light Gn, sequentially. Thereby, the Bp image signal, the Gp image signal, and the Rp image signal are obtained. Based on the image signals, in the same manner as that of the first embodiment, the concentration of the yellow pigment is calculated, and the prescribed exposure amount for the second preliminary imaging is calculated.

Further, in the second preliminary imaging, each time the observation target is illuminated with the second blue light BL and the green narrowband light Gn, sequentially, an image of the observation target is captured by the image capturing sensor 108. Thereby, the Bq image signal, the Gq image signal, and the Rq image signal are obtained. Based on the image signals, in the same manner as that of the first embodiment, the arithmetic value is calculated.

Incidentally, although the light source 20 is provided with the LEDs of four colors, i.e., the BS-LED 20a, the BL-LED 20b, the G-LED 20c, and the R-LED 20d in the above embodiment, the light source 20 may have other LEDs. For example, the light source 20 may be provided with a V-LED (Violet Light Emitting Diode) which emits violet light V at the wavelength band in the range of 380 nm to 420 nm with the center wavelength of 405 nm, in addition to the LEDs 20a to 20d. In an image signal obtained by capturing an image of the observation target illuminated by the violet light V with the center wavelength of 405 nm, there is much information about superficial-layer blood vessels each having an extremely short distance from the mucous membrane of the observation target. The superficial-layer blood vessels are information useful for diagnosis of lesion such as cancer. Since the oxygen saturation image in which the superficial-layer blood vessels are represented is generated based on the image signal obtained by capturing an image of the observation target illuminated with the violet light V, it is possible to provide a doctor with information useful for the diagnosis of lesion such as cancer.

Moreover, the second blue light BL at the wavelength band of 470±10 nm is emitted from the BL-LED 20b in the above embodiment. However, alternatively, the second blue light BL may be emitted from the B-LED which emits the blue light B at the wavelength band in the range of 420 nm to 500 nm with the center wavelength of 460 nm and a wavelength band restricting section through which the blue light B at a specific wavelength band is transmitted. For example, the wavelength band restricting section may be disposed on a light path of the B-LED, so as to cut the blue light B emitted from the B-LED at a short wavelength side, i.e., at the wavelength of less than 460 nm, and transmit the B-LED at a long wavelength side, i.e., at the wavelength of equal to or more than 460 nm. The light thus generated at the wavelength of not less than 460 nm to not more than 500 nm may be used as the second blue light BL.

Moreover, the wavelength band restricting section may be configured to cut the blue light B at the wavelength of equal to or more than 460 nm from the blue light B at the wavelength band in the range of 420 nm to 500 nm emitted from the B-LED, and transmit the blue light B at the wavelength of less than 460 nm. Then, the light thus generated at the wavelength of not less than 420 nm to less than 460 nm may be used as the first blue light BS.

Note that, the first blue light BS at the wavelength band of 450±10 nm is used in the above embodiment. However, alternatively, the light at the wavelength band in which the absorption coefficient of the oxygenated hemoglobin and the absorption coefficient of the reduced hemoglobin are the same and the absorption coefficient of the yellow pigment is relatively higher than those at other wavelength bands may be used. For example, instead of the first blue light BS, the green narrowband light at the wavelength band of 500±10 nm may be used.

Incidentally, the image generator 88 performs gain multiplication for pseudo coloring only for the low-oxygen region in the above embodiment, however, the image generator 88 may perform gain multiplication for pseudo coloring for the high-oxygen region in accordance with the oxygen saturation level, such that the entire oxygen saturation image is turned into a pseudo color. Further, the low-oxygen region and the high-oxygen region are distinguished from each other at the oxygen saturation level of 60% as the border. However, the border may be arbitrarily determined.

Although the present invention has been fully described by way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:
1. An endoscope system comprising:
a light source for emitting first light at a first wavelength band in which a light absorption amount changes in accordance with a concentration of yellow pigment contained in an observation target, and second light at a second wavelength band in which a light absorption amount changes in accordance with an oxygen saturation level of hemoglobin contained in the observation target and the light absorption amount also changes in accordance with the concentration of the yellow pigment, the second wavelength band being longer than the first wavelength band;

an image capturing sensor for capturing an image of the observation target;

a control section for controlling at least one of the light source and the image capturing sensor, so as to perform first preliminary imaging for imaging the observation target illuminated with the first light for the first preliminary imaging and perform second preliminary imaging for imaging the observation target illuminated with the second light for the second preliminary imaging;

a yellow pigment concentration calculator for calculating the concentration of the yellow pigment based on a first image signal obtained by performing the first preliminary imaging;

a prescribed exposure amount calculator for calculating a prescribed exposure amount of the second light in the second preliminary imaging based on the calculated concentration of the yellow pigment;

an arithmetic value calculator for performing a specific calculation based on a second image signal obtained by performing the second preliminary imaging in accordance with the prescribed exposure amount of the second light, so as to calculate an arithmetic value; and a determination section for determining whether or not the arithmetic value has become closer to an optimum value specified in advance.

2. The endoscope system according to claim 1, wherein
the control section performs main imaging for capturing an image of the observation target illuminated with the second light for the main imaging in accordance with the prescribed exposure amount of the second light in the case where it is determined that the arithmetic value has become closer to the optimum value, an oxygen saturation level calculator calculates the oxygen saturation level based on a third image signal obtained by performing the main imaging, and an image generator generates an oxygen saturation image in which the oxygen saturation level is represented based on the oxygen saturation level calculated by the oxygen saturation level calculator and the third image signal.

3. The endoscope system according to claim 2 further comprising a mode switching section for switching to an oxygen saturation mode for calculating the oxygen saturation level and generating the oxygen saturation image, wherein
the control section performs the first preliminary imaging and the second preliminary imaging in the case where the switching to the oxygen saturation mode is performed.

4. The endoscope system according to claim 2 further comprising a still-image acquisition instructing section for outputting instructions for acquiring the oxygen saturation image as a still image, wherein
the control section performs the first preliminary imaging and the second preliminary imaging in the case where the instructions for acquiring the still image are outputted.

5. The endoscope system according to claim 2, wherein
the control section performs the first preliminary imaging and the second preliminary imaging while a moving image of the observation target based on the oxygen saturation image is displayed.

6. The endoscope system according to claim 2, wherein
the control section controls such that an illumination time for illuminating the observation target in the first preliminary imaging and the second preliminary imaging is shorter than an illumination time for illuminating the observation target in the main imaging.

7. The endoscope system according to claim 1, wherein
the image capturing sensor includes a plurality of pixels containing specific pixels each of which is sensitive to at least one of the first wavelength band and the second wavelength band, and
the control section reads out a signal from the specific pixels without reading a signal from pixels other than the specific pixels among a plurality of the pixels in the case where the first preliminary imaging and the second preliminary imaging are performed.

8. The endoscope system according to claim 1, wherein
the control section controls at least one of a light emission amount of the second light in the second preliminary imaging and an exposure time of the image capturing sensor in the second preliminary imaging in accordance with the prescribed exposure amount of the second light.

9. The endoscope system according to claim 8, wherein
the prescribed exposure amount calculator increases the prescribed exposure amount of the second light in the second preliminary imaging, as the concentration of the yellow pigment calculated by the yellow pigment concentration calculator becomes higher.

10. The endoscope system according to claim 1, wherein
the optimum value is a value obtained in the case where the observation target does not have the yellow pigment.

11. The endoscope system according to claim 1, wherein
the light source emits third light at a third wavelength band in which a light absorption amount changes in accordance with a blood volume, the third wavelength band being longer than each of the first wavelength band and the second wavelength band,
the control section captures an image of the observation target illuminated with the first light for the first preliminary imaging and the third light in the first preliminary imaging, and captures an image of the observation target illuminated with the second light for the second preliminary imaging and the third light in the second preliminary imaging,
the prescribed exposure amount calculator calculates the prescribed exposure amount of at least one of the second light and the third light in the second preliminary imaging, and
the arithmetic value calculator calculates the arithmetic value based on the second image signal obtained by performing the second preliminary imaging in accordance with the prescribed exposure amount of at least one of the second light and the third light.

12. The endoscope system according to claim 11, wherein
the specific calculation is to calculate a signal ratio of an image signal obtained by capturing an image of the observation target illuminated with the second light to an image signal obtained by capturing an image of the observation target illuminated with the third light out of the second image signal obtained by performing the second preliminary imaging.

13. The endoscope system according to claim 11, wherein
the control section causes the first light and the third light to be emitted in a sequential manner in the first preliminary imaging, and causes the second light and the third light to be emitted in a sequential manner in the second preliminary imaging.

14. The endoscope system according to claim 11, wherein the control section causes the first light and the third light to be emitted at the same time in the first preliminary imaging, and causes the second light and the third light to be emitted at the same time in the second preliminary imaging.

15. The endoscope system according to claim 11, wherein the third light is narrowband light.

16. The endoscope system according to claim 15, wherein the third light is generated by restricting a wavelength band of the broadband light.

17. The endoscope system according to claim 11, wherein the prescribed exposure amount calculator decreases the prescribed exposure amount of the third light in the second preliminary imaging, as the concentration of the yellow pigment calculated by the yellow pigment concentration calculator becomes higher.

18. The endoscope system according to claim 11, wherein the first wavelength band includes an isosbestic wavelength at which oxygenated hemoglobin and reduced hemoglobin have the same absorption coefficient.

19. The endoscope system according to claim 18, wherein the first wavelength band is 450±10 nm, the second wavelength band is 470±10 nm, and the third wavelength band is 540±20 nm.

20. A method for operating an endoscope system comprising the steps of:
    emitting first light at a first wavelength band in which a light absorption amount changes in accordance with a concentration of yellow pigment contained in an observation target, and second light at a second wavelength band in which a light absorption amount changes in accordance with an oxygen saturation level of hemoglobin contained in the observation target and the light absorption amount also changes in accordance with the concentration of the yellow pigment, from a light source, the second wavelength band being longer than the first wavelength band;
    capturing an image of the observation target by an image capturing sensor;
    controlling at least one of the light source and the image capturing sensor by a control section, so as to perform first preliminary imaging for capturing an image of the observation target illuminated with the first light for the first preliminary imaging and perform second preliminary imaging for capturing an image of the observation target illuminated with the second light for the second preliminary imaging;
    calculating the concentration of the yellow pigment based on a first image signal obtained by performing the first preliminary imaging by a yellow pigment concentration calculator;
    calculating a prescribed exposure amount of the second light in the second preliminary imaging based on the calculated concentration of the yellow pigment by a prescribed exposure amount calculator;
    performing a specific calculation based on a second image signal obtained by performing the second preliminary imaging in accordance with the prescribed exposure amount of the second light so as to calculate an arithmetic value by an arithmetic value calculator; and
    determining whether or not the arithmetic value has become closer to an optimum value specified in advance by a determination section.

* * * * *